_US006030340A_

United States Patent [19]
Maffei et al.

[11] Patent Number: 6,030,340
[45] Date of Patent: Feb. 29, 2000

[54] SURGICAL RETRACTOR

[75] Inventors: Frank C. Maffei, Shelton; Thomas R. Hessler, Bethel, both of Conn.

[73] Assignee: United States Surgical, Norwalk, Conn.

[21] Appl. No.: 09/114,591

[22] Filed: Jul. 13, 1998

Related U.S. Application Data

[63] Continuation-in-part of application No. 08/994,686, Dec. 19, 1997.
[60] Provisional application No. 60/045,487, May 2, 1997.

[51] Int. Cl.[7] ................................................. A61B 17/02
[52] U.S. Cl. .......................................... 600/233; 600/228
[58] Field of Search .................................. 600/228, 227, 600/231, 232, 233

[56] References Cited

U.S. PATENT DOCUMENTS

| | | | |
|---|---|---|---|
| 2,594,086 | 4/1952 | Smith . | |
| 2,670,731 | 3/1954 | Zoll et al. | 600/232 |
| 3,998,217 | 12/1976 | Trumbull et al. | 600/233 |
| 4,254,763 | 3/1981 | McCready et al. | 600/231 |
| 4,421,107 | 12/1983 | Estes et al. | 600/233 |
| 4,457,300 | 7/1984 | Budde | 600/233 |
| 4,510,926 | 4/1985 | Inaba | 600/231 |
| 4,865,019 | 9/1989 | Phillips | 600/232 |
| 4,989,587 | 2/1991 | Farley | 600/232 |
| 5,067,477 | 11/1991 | Santangelo | 600/222 |
| 5,503,611 | 4/1996 | Jako | 600/201 |
| 5,779,629 | 7/1998 | Hohlen | 600/233 |
| 5,882,299 | 3/1999 | Rastegar et al. . | |

FOREIGN PATENT DOCUMENTS

| | | |
|---|---|---|
| 0336526 | 10/1989 | European Pat. Off. . |
| 2102681 | 2/1983 | United Kingdom . |

Primary Examiner—Paul J. Hirsch

[57] ABSTRACT

A surgical retractor assembly is provided comprising a frame having first and second portions, a first hook member supported on the frame, a second hook member supported on the frame and movable with respect to the frame, a ring member removably mounted on the frame and configured to engage at least one surgical instrument for use in performing a surgical procedure, and a frame support supporting the frame. The frame support is adapted to retain the first portion of the frame in a selected raised position with respect to the second portion of the frame. The frame support preferably comprises an elongated shaft having a locking mechanism for locking the frame in the selected raised position.

26 Claims, 26 Drawing Sheets

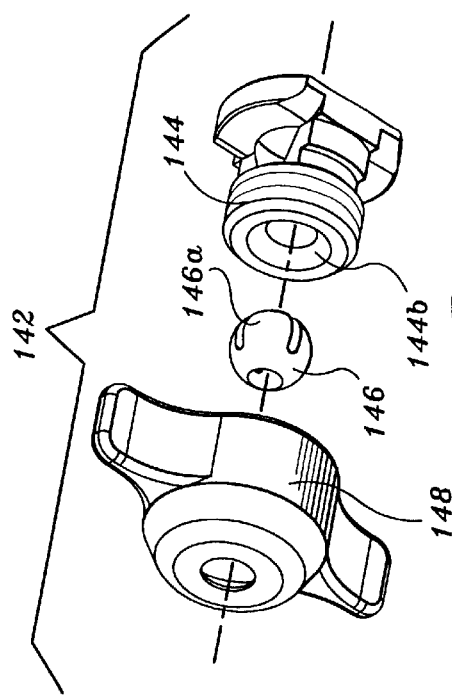
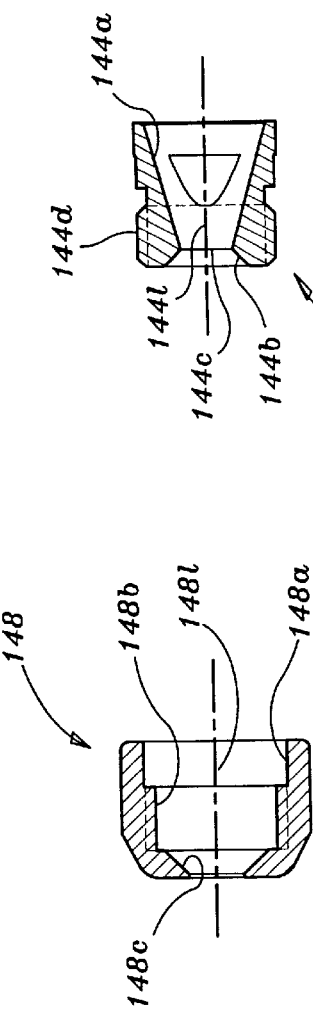
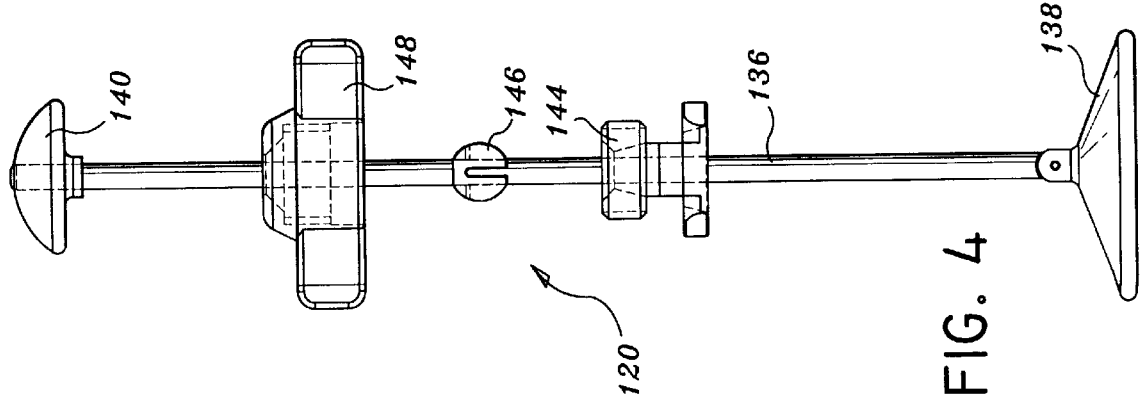

SURGICAL RETRACTOR

CROSS REFERENCE TO RELATED APPLICATIONS

This application is a continuation-in-part of U.S. application Ser. No. 08/994,686 filed Dec. 19, 1997 which, in turn, claims priority to U.S. Provisional Application Ser. No. 60/045,487 filed May 2, 1997.

BACKGROUND

1. Technical Field

The disclosure relates to a surgical apparatus and method and more particularly to a surgical apparatus and method for retracting tissue and/or bone.

2. Background of the Related Art

The diagnosis and treatment of coronary disease and related conditions typically require access to the heart, blood vessels, and associated tissue. Such procedures include cardiopulmonary bypass, valve repair and replacement, and treatment of aneurysms. Until recently, access to the patient's thoracic cavity was achieved by a large longitudinal incision in the chest. This procedure, referred to as a median sternotomy, required a saw or other cutting instrument to cut the sternum and allow two opposing halves of the rib cage to be spread apart. U.S. Pat. No. 5,025,779 to Bugge discloses a retractor which is designed to grip opposite sternum halves and spread the thoracic cavity apart. The large opening which is created by this technique enables the surgeon to directly visualize the surgical site and perform procedures on the affected organs. However, such procedures that involve large incisions and substantial displacement of the rib cage are often traumatic to the patient with significant attendant risks. The recovery period may be extended and is often painful. Furthermore, patients for whom coronary surgery is indicated may need to forego such surgery due to the risks involved with gaining access to the heart.

To avoid the risks and pitfalls of median sternotomies, a minimally invasive "window" approach to vascular or cardiac surgery has been developed. One example of the window approach is disclosed in European patent application 97106912.5, filed Apr. 25, 1997. The 97106912.5 application shows a ring shaped retractor having a series of retractor blades mounted thereon to spread the ribs and allow access to the heart for performing procedures such as coronary bypass.

In certain instances, additional access to other vessels and improved visibility is desirable. One way to achieve this would be to not only spread the retractor blades apart to spread the ribs laterally, but to also spread the ribs and surrounding upwardly away from the body, e.g. to lift the tissue. This would enable additional procedures to be performed through a window approach, such as an "IMA (internal mammary artery) takedown" where the artery is dissected for subsequent attachment to the heart or other vessel to complete the bypass. Furthermore, an apparatus and procedure are needed which provide a stable framework for supporting additional instruments which may be used during these procedures, while still providing the appropriate access.

SUMMARY

The apparatus and method disclosed herein provides improved surgical access through a minimally invasive window approach. This is achieved by providing a surgical retractor assembly comprising a frame lying in first plane at least one elevation control supporting the frame and configured to selectively lift at least a portion of the frame out of the first plane; and at least one hook member supported on the frame and configured to retract tissue. A second hook member is preferably removably mounted to the frame and configured to retract tissue in a direction away from the at least one hook member. The elevation control assembly may comprise pair of elongated shafts removably mounted to the frame, each of the control assemblies including a locking mechanism to retain the frame in the selected position.

A surgical retractor assembly is also provided comprising a frame, a first hook member supported on the frame, a second hook member supported on the frame and movable with respect to the frame, and a frame support supporting the frame and adapted to retain a first portion of the frame in a selected raised position with respect to a second portion of the frame.

A method for accessing the internal mammary artery in a minimally invasive procedure is also provided comprising placing a first hook member supported on a frame between the ribs, placing a second hook member supported on the frame between the ribs, moving the second hook member in a direction away from the first hook member to retract the ribs, elevating a first portion of the frame away from the body to a selected raised position, and retaining the first portion of the frame in the selected raised position. The method may further comprise the step of inserting a dissector through an opening in the in the frame to dissect the internal mammary artery. The step of elevating the first portion of the frame may comprise the step of manually sliding the first portion along first and second spaced apart shafts.

A surgical retractor is also provided which has a substantially planar frame defining an opening for overlying an operative site on a patient, and at least one retractor blade slidably mounted on the frame. The frame is positioned on the patient such that an opening therein overlies the operative site, and a ring, which is configured and dimensioned corresponding to the frame, is removably attached to the frame. The operative site is percutaneously accessed through the opening. Obstructing tissue and/or bones are retracted and/or lifted by the surgical retractor to create an opening to provide access for the surgical procedure. Surgical instruments are provided which are engageable with the ring and operable at the operative site. A surgical procedure is carried out through the common opening in the ring and the frame, with the surgical instruments.

BRIEF DESCRIPTION OF THE DRAWINGS

Various embodiments of the presently disclosed surgical retractor apparatus are described herein with reference to the drawing figures wherein:

FIG. 4 is a side view of an elevation control assembly of the surgical retractor of FIG. 1;

FIG. 5 is a perspective view with parts separated of the locking mechanism of the elevation control assembly of FIG. 4;

FIG. 6 is a cross-sectional view of a knob-nut of the locking mechanism of FIG. 5;

FIG. 7 is a cross-sectional of the collet of the locking mechanism of FIG. 5;

DETAILED DESCRIPTION OF PREFERRED EMBODIMENTS

The preferred embodiments of the apparatus disclosed herein will be discussed in terms of procedures and apparatus for use in heart surgery. More specifically, the apparatus can be used to enable minimally invasive dissection of the internal mammary artery (IMA) by retracting the ribs to enable access to the IMA. However, the present disclosure should not be limited to an apparatus for use in conjunction with such heart surgery, but may find application in surgery wherein access to the surgical site is achieved through a small incision and retraction of the surrounding tissues and/or bone if desired.

Figure 2:
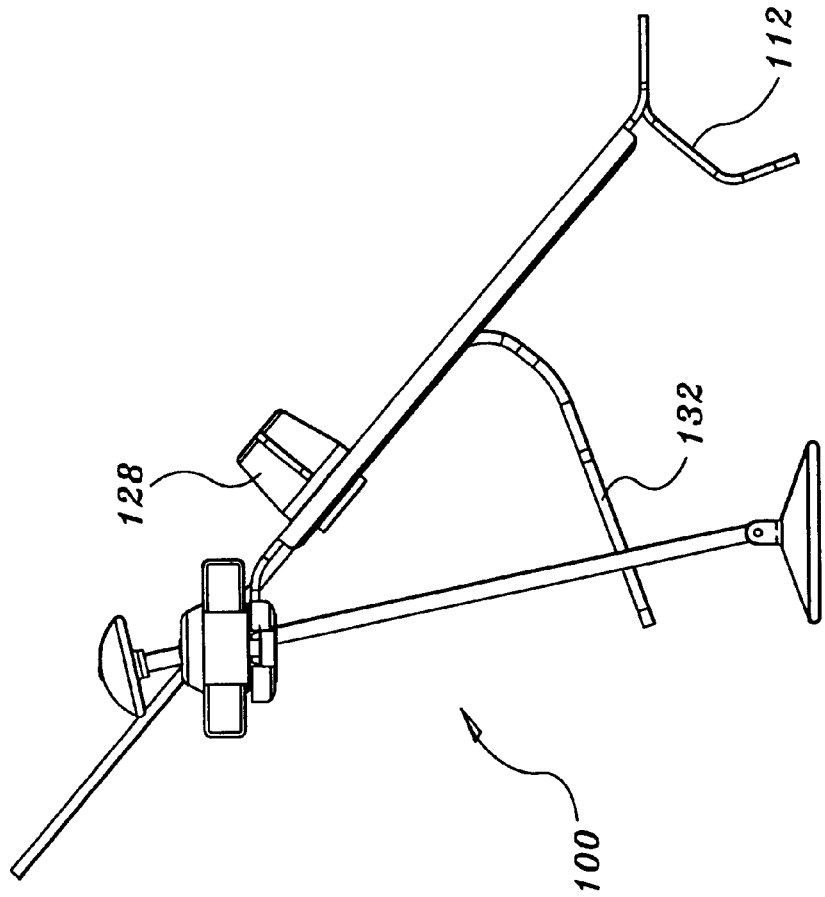
FIG. 2 is a side view of the surgical retractor of FIG. 1.
Figure 1:
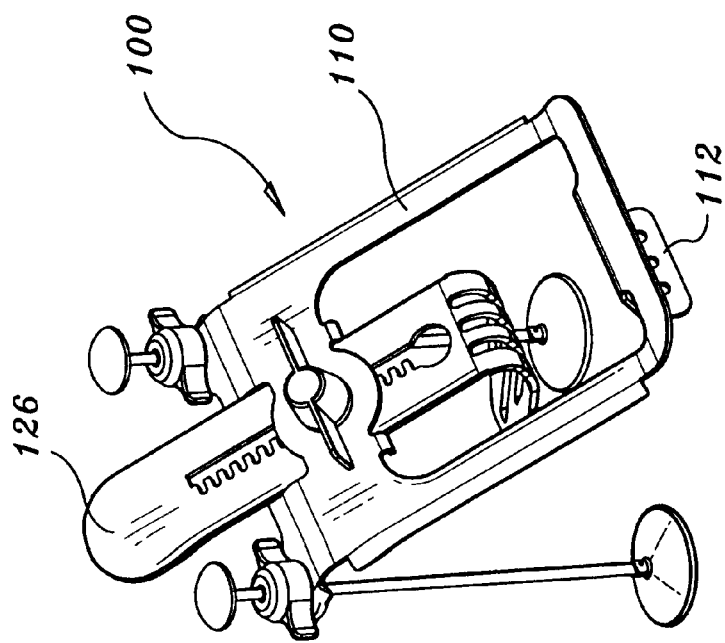
FIG. 1 is a perspective view of a surgical retractor constructed in accordance with a first embodiment of the present disclosure.
Figure 3:
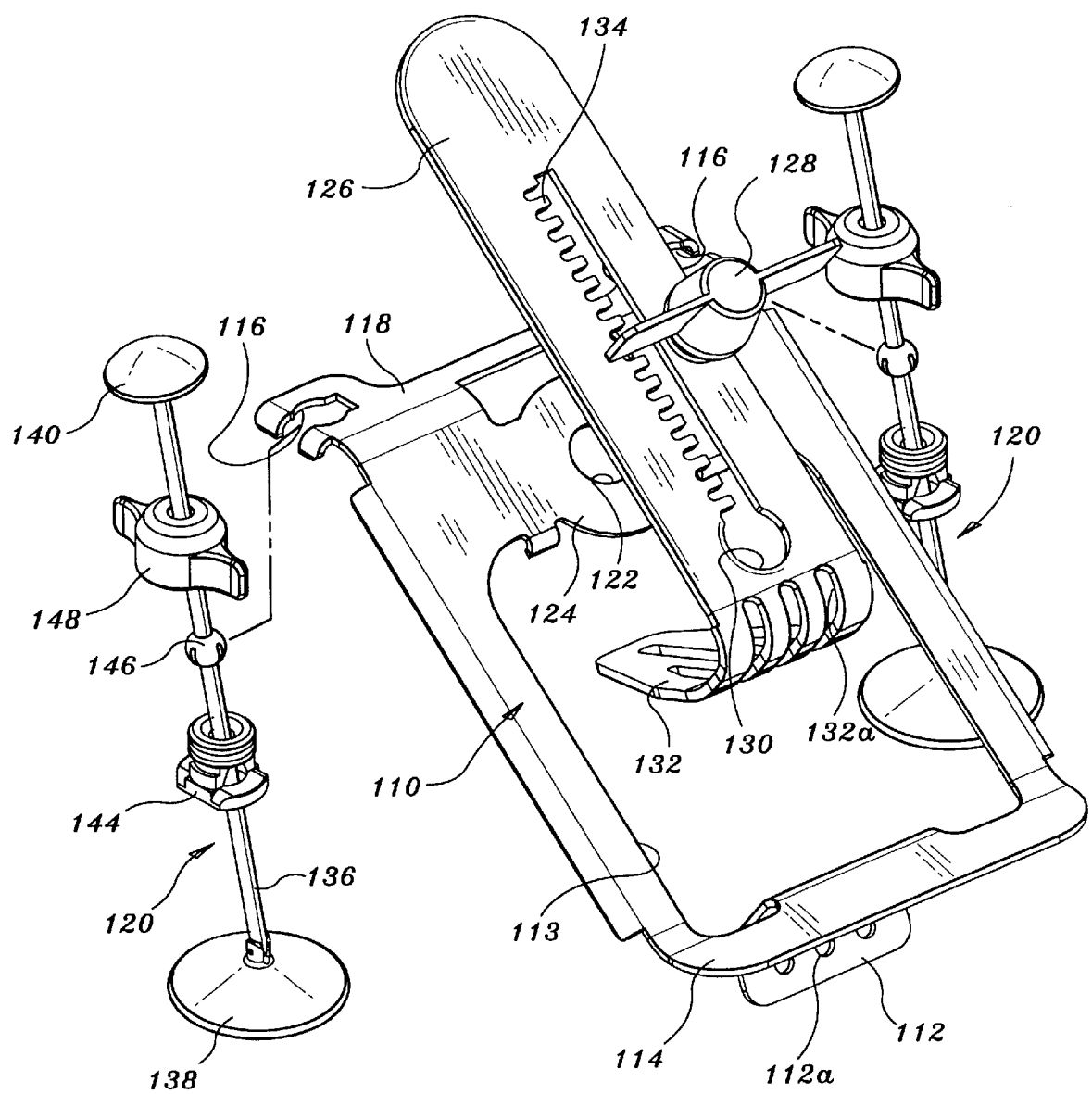
FIG. 3 is an enlarged perspective view with parts separated of the surgical retractor of FIG. 1.
Figure 9:
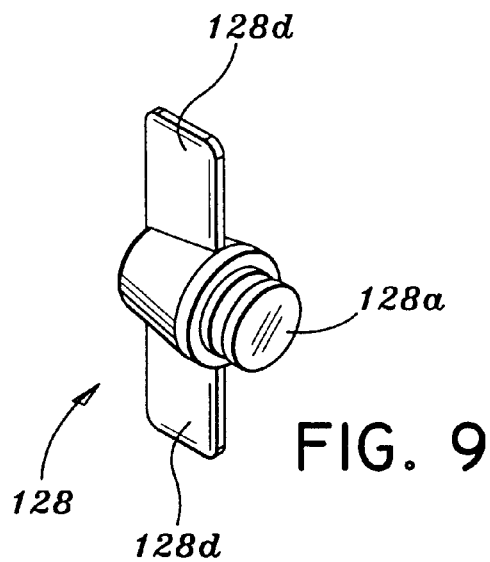
FIG. 9 is a perspective view of the adjustment knob for the adjustable hook of FIG. 8.
Figure 8:
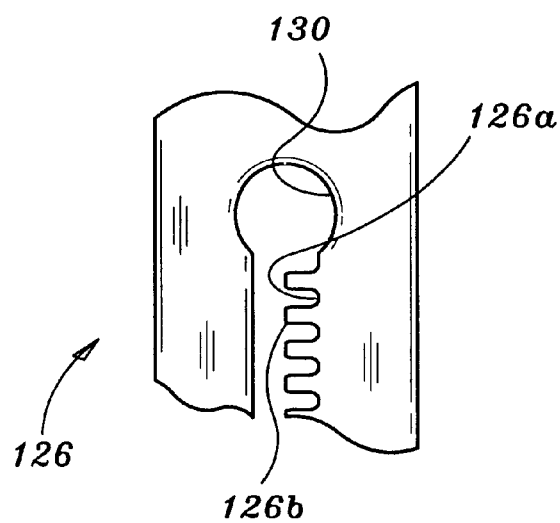
FIG. 8 is a partial view of the adjustable hook member of the surgical retractor apparatus of FIG. 1.
Figure 10:
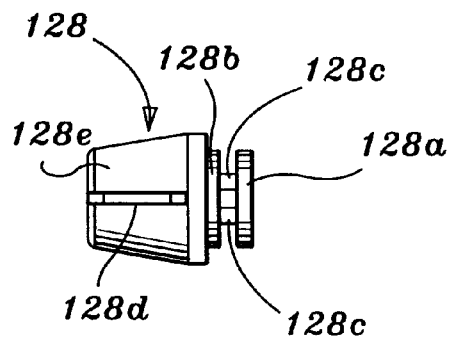
FIG. 10 is a side view of the adjustment knob of FIG. 9.
Figure 11:
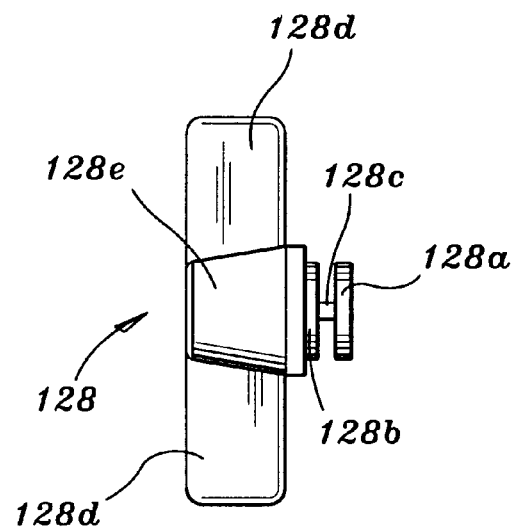
FIG. 11 is a side view of the adjustment knob of FIGS. 9 and 10 taken orthogonally from the view shown in FIG. 10.

Referring now in detail to the drawings in which like reference numerals identify similar or identical elements, a first embodiment of the surgical retractor of the present disclosure is illustrated in FIGS. 1–3, and is designated generally by reference numeral 100. Surgical retractor 100 has frame member 110 which is preferably formed of a material which is readily sterilizable after use, for example, stainless steel. Alternatively, some or all of the components may be made of disposable materials so that the apparatus could be discarded after use. Frame 110 has various cut-out portions and contours which may be formed by way of stamping frame 110 out of a solid sheet of material.

A fixed hook portion 112 is provided at the lower flattened end portion 114 of frame member 110. Hook portion 112 is preferably provided with slotted openings 112a to facilitate gripping of bone and/or tissue, thereby preventing lateral movement of hook member 126. Alternatively, slotted openings 112a may either be replaced by or supplemented with rib portions (similar to ribs 212d shown in FIGS. 16–18 and described further herein) formed on the tissue contacting areas of hook portion 112. Cut-out portions 116 are formed at the upper end 118 of frame member 110 to receive a pair of elevation control assemblies 120 therein. Circular cut-out 122 is provided in central portion 124 of frame 110 to attach an adjustable hook member 126 by way of an adjustment knob 128 passing through cut-out 130 formed at the bottom of adjustable hook member 126. Adjustable hook member 126 is further provided with hook portion 132 which curves inwardly through the central opening formed by frame 110. Hook portion 132 is preferably provided with slotted openings 132a to facilitate gripping of bone and/or tissue, thereby preventing lateral movement of hook member 126. Alternatively, slotted openings 132a may either be replaced by or supplemented with rib portions (similar to ribs 212d shown in FIGS. 16–18) formed on the tissue contacting areas of hook portion 132. A rack portion 134 is formed longitudinally along the main surface of adjustable hook member 126.

A large central opening is provided and is defined by inner edge 113. This opening allows the surgeon to insert various surgical instruments through frame member 110 to perform surgical procedures. For example, in the case of a minimally invasive heart bypass procedure, dissectors can be inserted to dissect the IMA for subsequent attachment to another artery.

Referring now to FIGS. 4–7, the structure and operation of elevation control assemblies 120 will now be discussed in detail. As shown in the assembled view of FIG. 4, elevation control assembly 120 includes an elongated shaft 136 pivotably mounted to a base portion 138 and having a dome-shaped knob 140 to facilitate gripping, attached to the top thereof. A locking mechanism 142, as shown in FIG. 5, is disposed on shaft 136 and includes a collet member 144, a compressible ball-shaped member 146 and a knob-nut 148. Each of these elements includes a central opening of sufficient diameter to permit them to slide along shaft 136 when spaced apart from each other. Knob-nut 148, as shown in FIG. 6, defines a stepped throughbore having adjacent cylindrical step portions 148a and 148b and a frusto-conical portion 148c, each of which are axially aligned along the central longitudinal axis 148L. Portion 148 includes threads formed thereon.

Referring to FIG. 7, collet member 144 includes a tapered throughbore formed by adjoining frusto-conical sections 144a and 144b which form neck portion 144c at their juncture. Sections 144a and 144b are axially aligned along the central longitudinal axis 144L of collet 144. External threads are formed on the outer surface 144d so as to mesh with the threads formed at step portion 148b of knob-nut 148.

Compressible ball 146 of elevation control assembly 120 includes flexible portions 146a, as shown in FIG. 5, which flex when ball 146 is compressed between frusto-conical surface 144b and frusto-conical surface 148c of the collet 144 and knob-nut 148, respectively. In this manner, when knob-nut 148 is threaded onto collet 144, ball 146 is compressed so that finger portions 146a are biased against shaft 136 so as to lock the locking mechanism 142 and prevent axial movement of the assembly along shaft 136. This locking action prevents axial movement of frame member 110 along shaft 136 as well thereby locking frame member 110 in a fixed position.

Referring to FIGS. 8–11, the adjustment feature of adjustable hook member 126 will now be described in detail. As mentioned above, adjustable hook member 126 includes a cut-out 130 which is configured and dimensioned to receive a circular base 128a of adjustment knob 128. Circular base 128a together with a second circular base 128b form a gap region which is slightly greater than the thickness of the plate material which forms adjustable hook member 126. In this manner, once circular base 128 is passed through cut-out 130, adjustment knob 128 may be slid along adjustable hook member 126 until post members 128c become seated in the first valley 126a which are formed by the gaps between teeth 126b disposed along one side of a longitudinal opening extending along adjustable hook member 126. To facilitate rotation of adjustment knob 128, link portions 128d are formed on opposite sides of hub portion 128e. In this manner, adjustable hook member 126 may be adjusted toward or away from fixed portion 112 by rotating adjustment knob 128 in the desired direction so that post members 128c bias against the sidewalls of teeth 126b and urge adjustable hook member 126 in the desired direction due to the fixed nature of adjustment knob 128 with respect to frame member 110.

In operation of the overall retractor 100, the frame member 110 with the adjustable hook member 126 disposed thereon is inserted between the structures desired to be retracted, for example, in the case of heart surgery the retractor hooks are inserted between the fourth and fifth ribs so that hook portion 132 biases against a first of these ribs and hook portion 112 biases against a second of these ribs in opposite directions. In this position, the retractor frame 112 is substantially parallel to the ribs. Adjustment knob 128 is turned clockwise in the embodiment shown in FIGS. 1–11 to retract hook portion 132 away from hook portion 112 until the desired opening is achieved between the adjacent ribs. The outwardly extending end 118 of frame 110 is then elevated by first loosening locking mechanism 142 on each of the elevation control assemblies 120 and raising end 118 of the frame member so as to elevate one side of the retractor 100.

Once the desired elevation is achieved, locking mechanism 142 is locked as described above to fix the axial location of frame end 118 relative to the shaft 136 of each of elevation control assemblies 120. After the surgical procedure is complete, surgical retractor 100 can be completely disassembled and sterilized for reuse.

Figure 12:
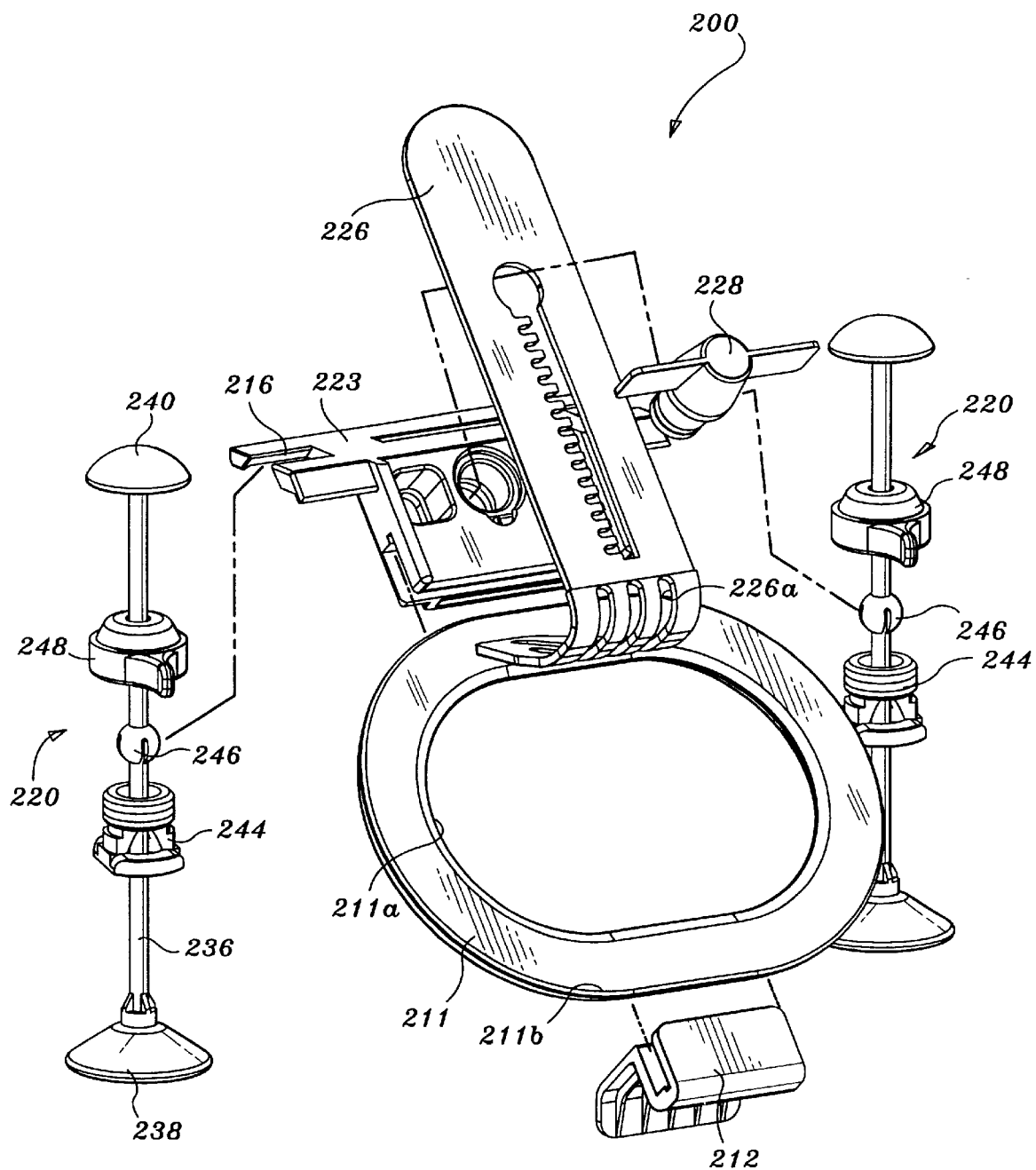
FIG. 12 is a perspective view of a surgical retractor apparatus constructed in accordance with a further embodiment of the present disclosure.

Referring to FIG. 12, a further embodiment of the surgical retractor of the present disclosure is designated generally by reference numeral 200. Preferably, surgical retractor 200 is a disposable assembly which may be discarded after use. Accordingly, the various components of surgical retractor 200 may be made of lightweight polycarbonate materials. However, it is also within the scope of the present disclosure that the various components of surgical retractor 200 may also be made of materials such as stainless steel which may be sterilized and reused if desired.

Surgical retractor 200 includes an oval shaped ring member 211 which defines an inner window area as defined by inner edge 211a. This window area, like the opening in frame member 110 of the previously described embodiment, allows the surgeon to insert various surgical instruments through ring member 211 to perform surgical procedures. Ring 211 further includes a peripheral lip 211b which extends outwardly along the upper outer periphery of ring member 211. Inner edge 211a is preferably beveled inwardly so as to define a smooth surface along the perimeter of the operating window. A removable hook member 212 is snap fitted onto ring member 211 along a first straight portion disposed on one side of ring member 211 and a base portion 223 is similarly snap fitted to a second straight portion disposed on the opposite side of ring member 211. Preferably, removable hook 212 and base 223 are molded parts, each of which will be described in further detail herein. An adjustable hook 226 is attached to base 223 by adjustment knob 228 which snap fits into base 223. Alternatively adjustment knob 228 may be threaded into base 223.

The operation of adjustable hook 226 is similar to that described above in connection with the embodiment of FIG. 1. Accordingly, that operation will not be described in further detail herein. However, it should be noted that adjustable hook 226 which has slotted openings 226a formed thereon to facilitate gripping of tissue and/or bone could be provided with projecting rib portions (similar to rib portions 212d described further herein) either in place of or in conjunction with slotted openings 226a.

A pair of vertical stabilizers 220 are also provided for surgical retractor 200 and are attached to base 223 in openings 216 formed on opposite ends of the base member. Unlike elevation control assemblies 120 of the previously described embodiment, vertical stabilizer members 220 are designed to hold base 223 and therefore, one side of ring member 211 at a fixed elevation relative to bases 238. Otherwise, collet 244, ball 246 and knob-nut 248 work in similar fashion as locking mechanism 142 in order to lock frame member 223 in position relative to the patient's chest wall. It should be noted, that ring member 211 is adapted to have various other instruments connected or attached thereto as desired.

Figure 13:
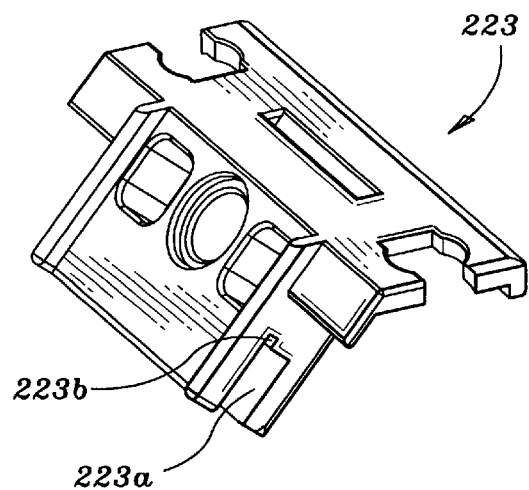
FIG. 13 is a perspective view of a base portion of the surgical retractor apparatus of FIG. 12.
Figure 14:
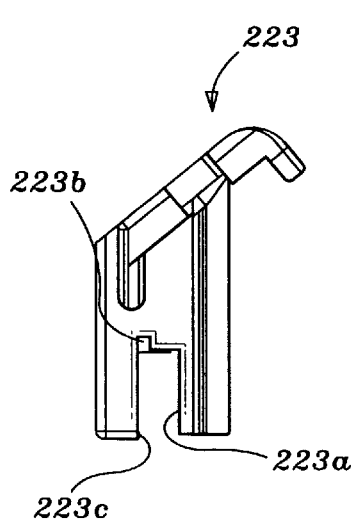
FIG. 14 is a side view of the base portion of FIG. 13.
Figure 15:
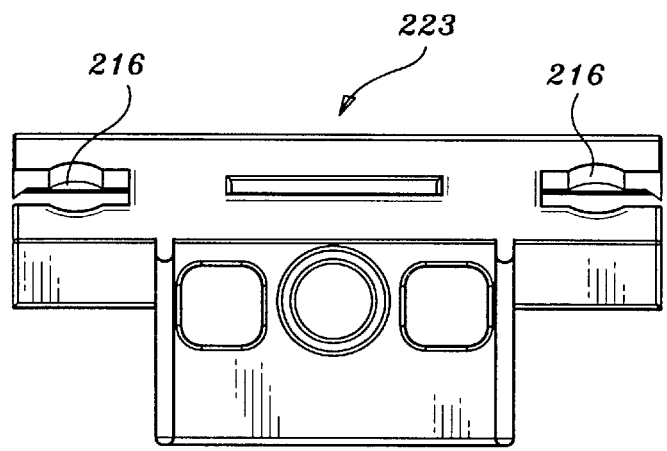
FIG. 15 is a front view of the base portion of FIG. 13.

Referring to FIGS. 13–15, base member 223 is shown having slot 223a formed therein with minor slot 223b formed at the top of slot 223a. Slot 223b facilitates receiving the lip 211b of ring member 211 and lip portion 223c facilitates snap fitting locking type arrangement of base 223 onto ring member 211. Alternatively, ring member 211 could have a peripheral groove formed thereon whereas base 223 and removable hook 212 could each have a projecting lip formed thereon which would facilitate attachment of these elements to ring member 211.

Figure 16:
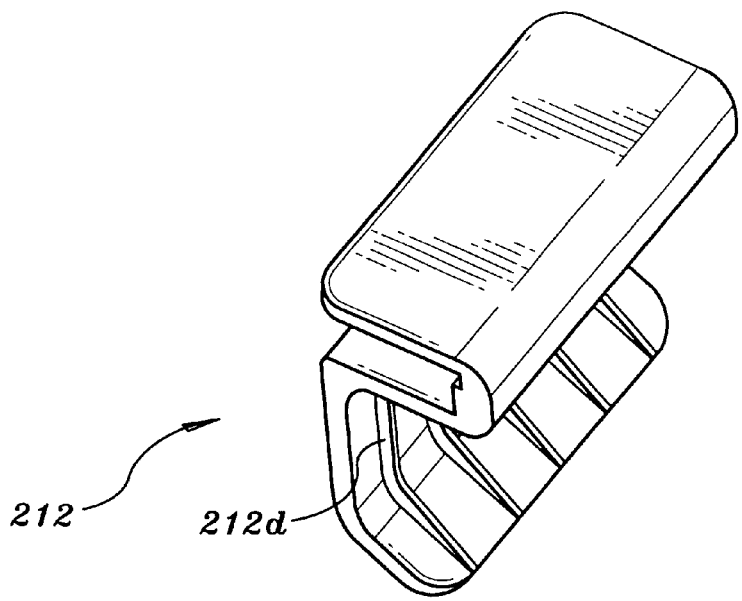
FIG. 16 is a perspective view of a removable base hook for the surgical retractor apparatus embodiment of FIG. 12.
Figures 17, 18:
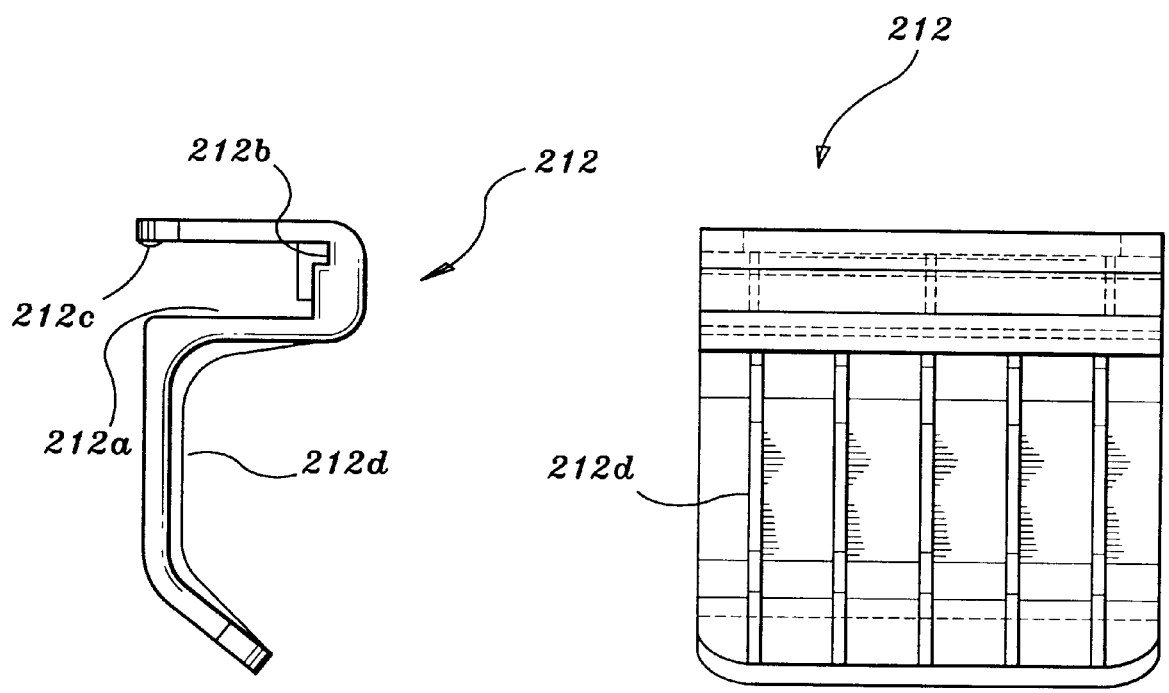
FIG. 17 is a side-view of the removable base hook of FIG. 16.
FIG. 18 is a front-view of the removable base hook of FIG. 16.
Figure 19:
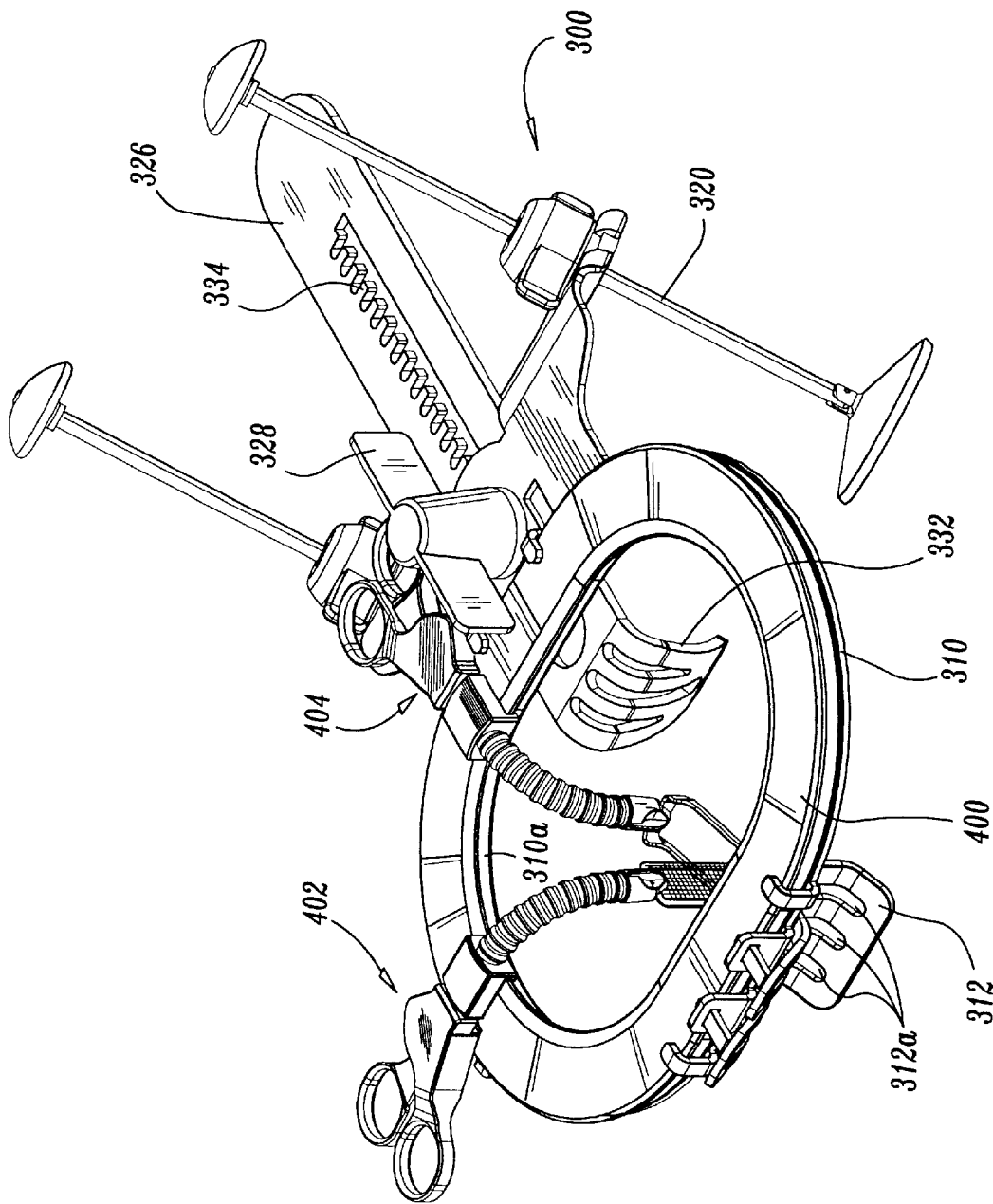
FIG. 19 is a perspective view of a surgical retractor constructed in accordance with another embodiment of the present disclosure having a ring and surgical instruments attached thereto.

Referring to FIGS. 16–18, removable hook 212 includes an elongated slot 212a formed therein and a minor slot 212b formed therein to facilitate attachment of removable hook member 212 to ring member 211 in a similar manner of attachment of base 223 thereto. Similarly, removable hook member 212 includes a raised surface portion 212c which facilitates the snap fitting of removable hook to the ring 11. Removable hook member 212 is provided with protruding rib portions 212d which extend outwardly from the body contacting surface of removable hook member 212. Rib portions 212d prevent lateral movement of the hook member relative to the contacted body portion, e.g., the rib section. Alternatively, rib portions 212d could be replaced with or supplemented by slotted openings to allow body tissue and/or bone to engage the openings.

Referring now to FIGS. 19–23, another embodiment of the surgical retractor in accordance with the present disclosure is illustrated having an oval shaped ring attached thereto and is designated generally by reference numeral 300.

Preferably, surgical retractor 300 is a disposable assembly which may be discarded after use. Accordingly, the various components of surgical retractor 300 may be made of lightweight polycarbonate materials. However, it is also within the scope of the present disclosure that the various components of surgical retractor 300 may also be made of materials such as stainless steel which may be sterilized and reused if desired.

Surgical retractor 300 includes an oval shaped frame member 310 which defines an inner window area as defined by inner edge 310a. This window area, like the openings in frame member 110 and oval shaped ring member 211 of the previously described embodiments, allows the surgeon to insert various surgical instruments through frame member 310 to perform surgical procedures.

A hook portion 312 is provided at a lower end portion 314 of frame member 310. Hook portion 312 is preferably provided with slotted openings 312a to facilitate gripping of bone and/or tissue, thereby preventing lateral movement thereof. Alternatively, slotted openings 312a may either be replaced by or supplemented with rib portions (similar to ribs 212d shown in FIGS. 16–18) formed on the tissue contacting areas of hook portion 312.

Figure 21:
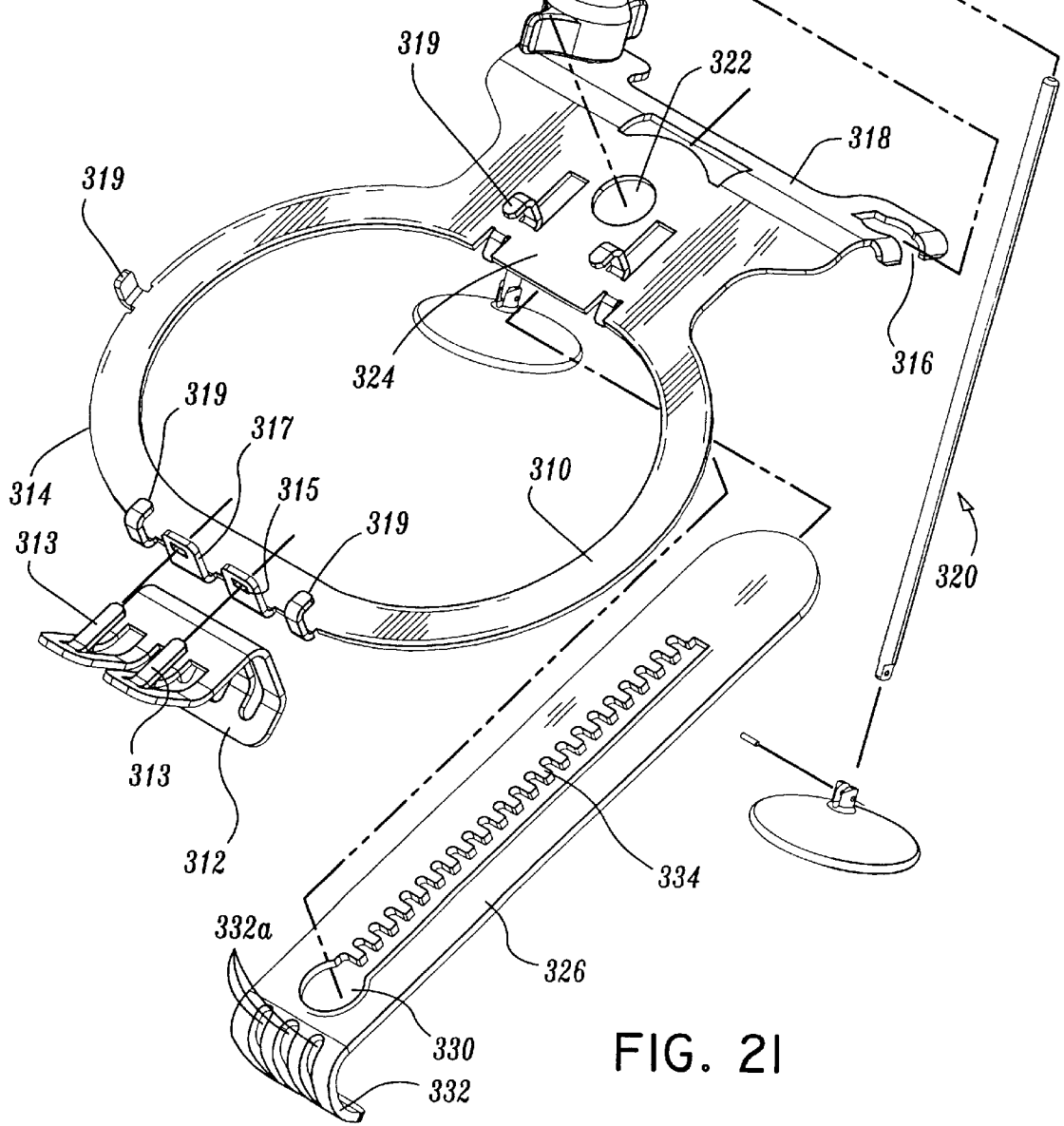
FIG. 21 is an exploded perspective view of the surgical retractor of FIG. 19.
Figure 23:
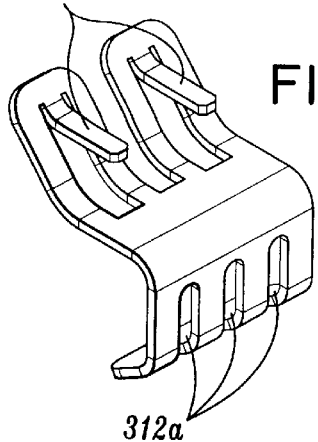
FIG. 23 is a perspective view of the fixed hook member of the surgical retractor of FIG. 19.
Figure 24:
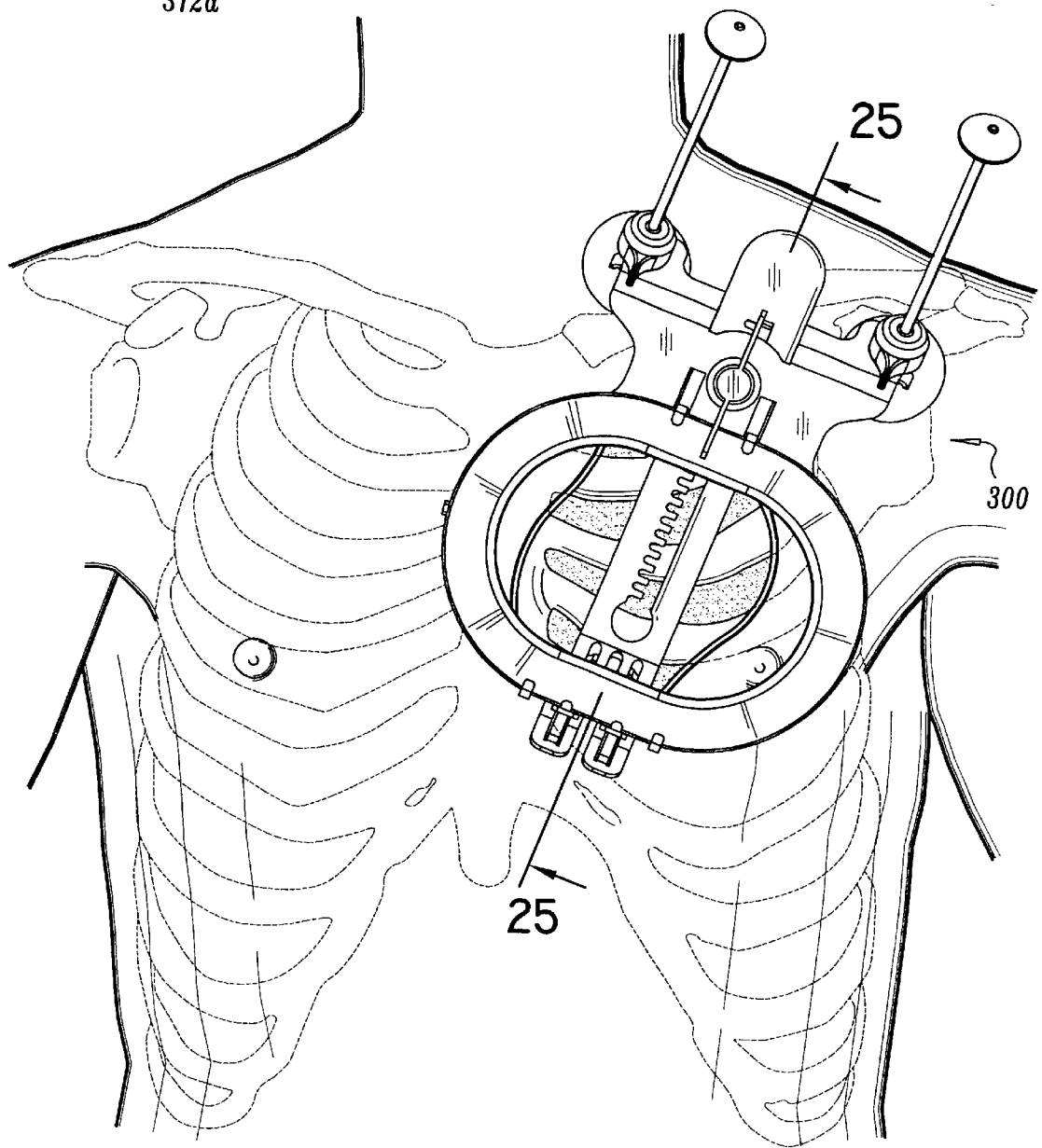
FIG. 24 is a top view of the surgical retractor positioned on the patient's chest.

As best seen in FIG. 21, hook portion 312 includes two tabs 313 extending outward therefrom which are configured and dimensioned to engage holes 315 formed in tabs 317 extending from lower end portion 314 of frame member 310. Tabs 313 may be positioned within holes 315 loosely or secured therein by an interference fit, epoxy, weld, by bending the tabs after they have been inserted through the holes, or by any other suitable means known to one having ordinary skill in the art.

Cut-out portions 316 are formed at the upper end 318 of frame member 310 to receive a pair of elevation control assemblies 320 therein. Circular cut-out 322 is provided in central portion 324 of frame 310 to attach adjustable hook member 326 by way of an adjustment knob 328 passing through cut-out 330 formed at the bottom of adjustable hook member 326. Adjustable hook member 326 is further provided with hook portion 332 which curves inwardly through the central opening formed by frame 310. Hook portion 332 is preferably provided with slotted openings 332a to facilitate gripping of bone and/or tissue, thereby preventing lateral movement of adjustable hook member 326. Alternatively, slotted openings 332a may either be replaced by or supplemented with rib portions (similar to ribs 212d shown in FIGS. 16–18) formed on the tissue contacting areas of hook portion 332. A rack portion 334 is formed longitudinally along the main surface of adjustable hook member 326.

An oval shaped ring member 400, which is dimensioned and configured corresponding to the shape of frame member 310, is removably attached to frame member 310. Frame member 310 includes tabs 319 extending from three sides to insertably receive and retain ring member 400. Preferably, ring member 400 is a disposable assembly which may be discarded after use. Accordingly, ring member 400 may be made of lightweight polycarbonate materials. However, it is also within the scope of the present disclosure that ring member 400 may also be made of materials such as stainless steel which may be sterilized and reused if desired.

Figure 20:
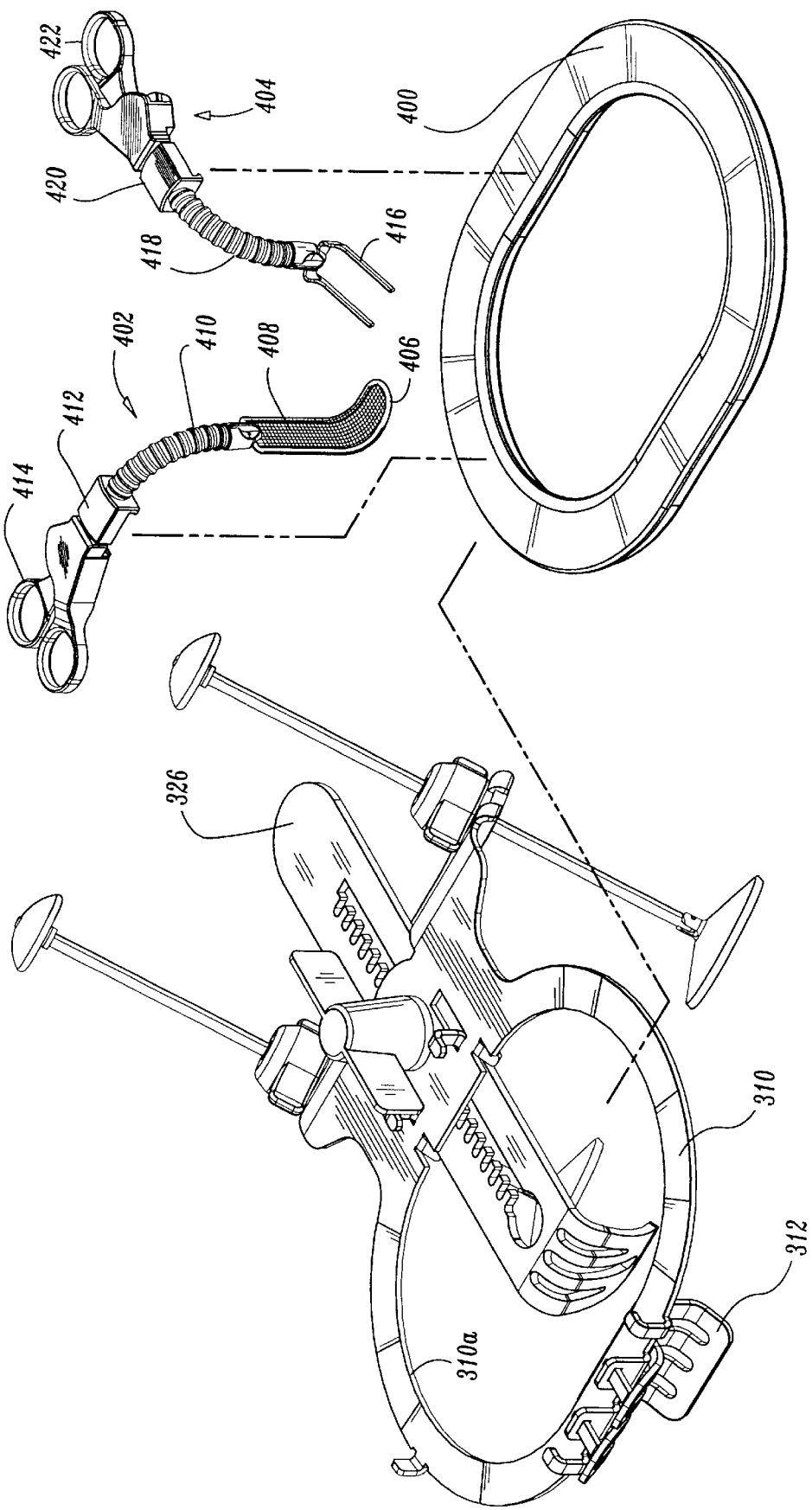
FIG. 20 is an exploded perspective view of the surgical retractor, ring, and surgical instruments of FIG. 19.
Figure 22:
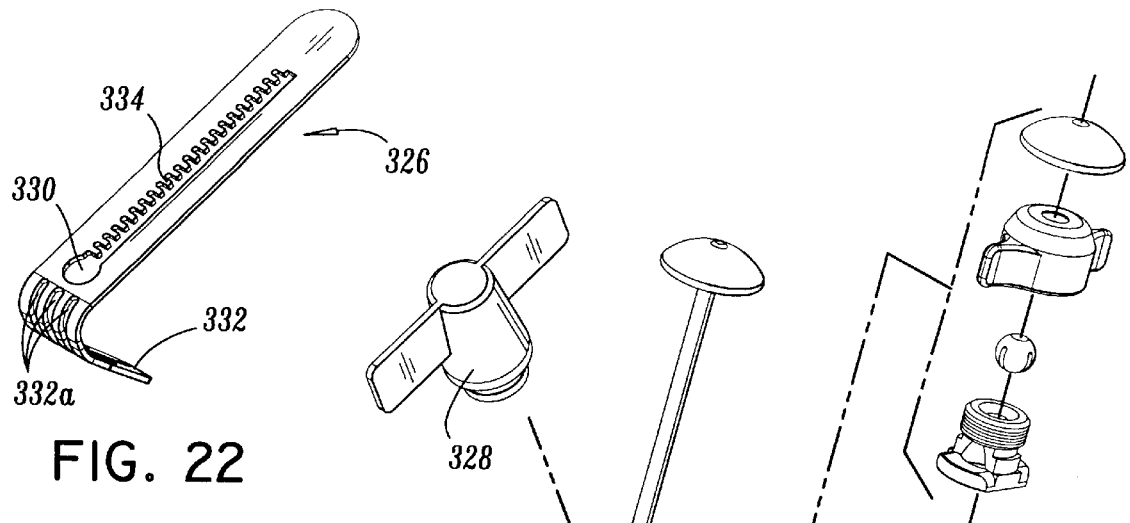
FIG. 22 is a perspective view of the adjustable hook member of the surgical retractor of FIG. 19.

Surgical instruments, such as a heart manipulator 402 or a heart stabilizer 404 are configured to be removably attached to ring member 400 and utilized during heart surgery. As best seen in FIG. 20, heart manipulator 402 generally includes a loop-shaped frame 406 that supports mesh surface 408. Frame 406 and mesh surface 408 together form a heart contacting surface for manipulating the heart therewith. An articulating arm 410 positioned between frame 406 and a mounting assembly 412 allows for articulation of mesh surface 408 within the opening of ring 400. Handle 414 enables the engagement and disengagement of mounting assembly 412 with ring member 400. Heart stabilizer 404 generally includes frame 416, articulating arm 418, and mounting assembly 420. Articulating arm 418 is configured to allow frame 416 to be positioned at the precise location and orientation with respect to the heart of the patient. Handle 422 enables the engagement and disengagement of mounting assembly 420 to ring member 400.

Figure 25:
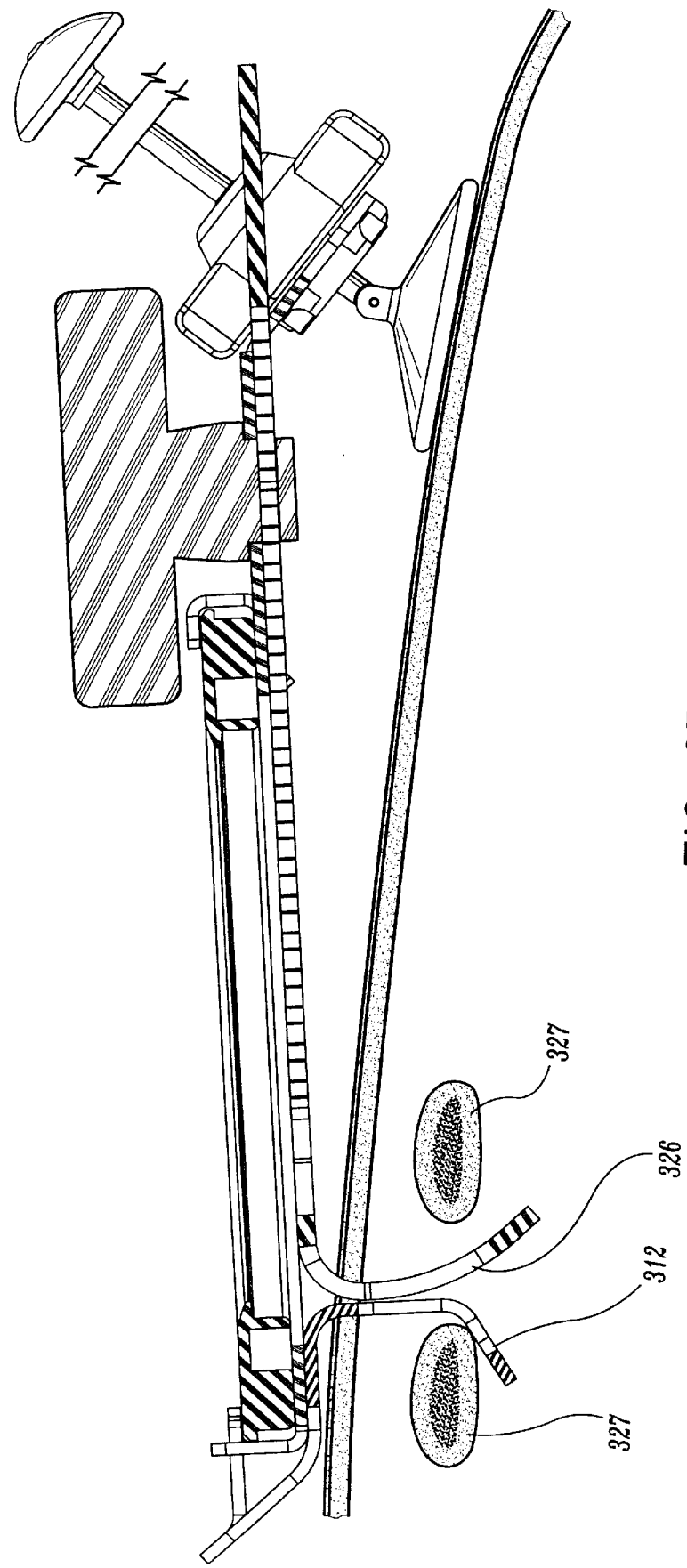
FIG. 25 is a cross-sectional view taken along line 25—25 of FIG. 24 of the surgical retractor positioned on the patient's chest.
Figure 26:
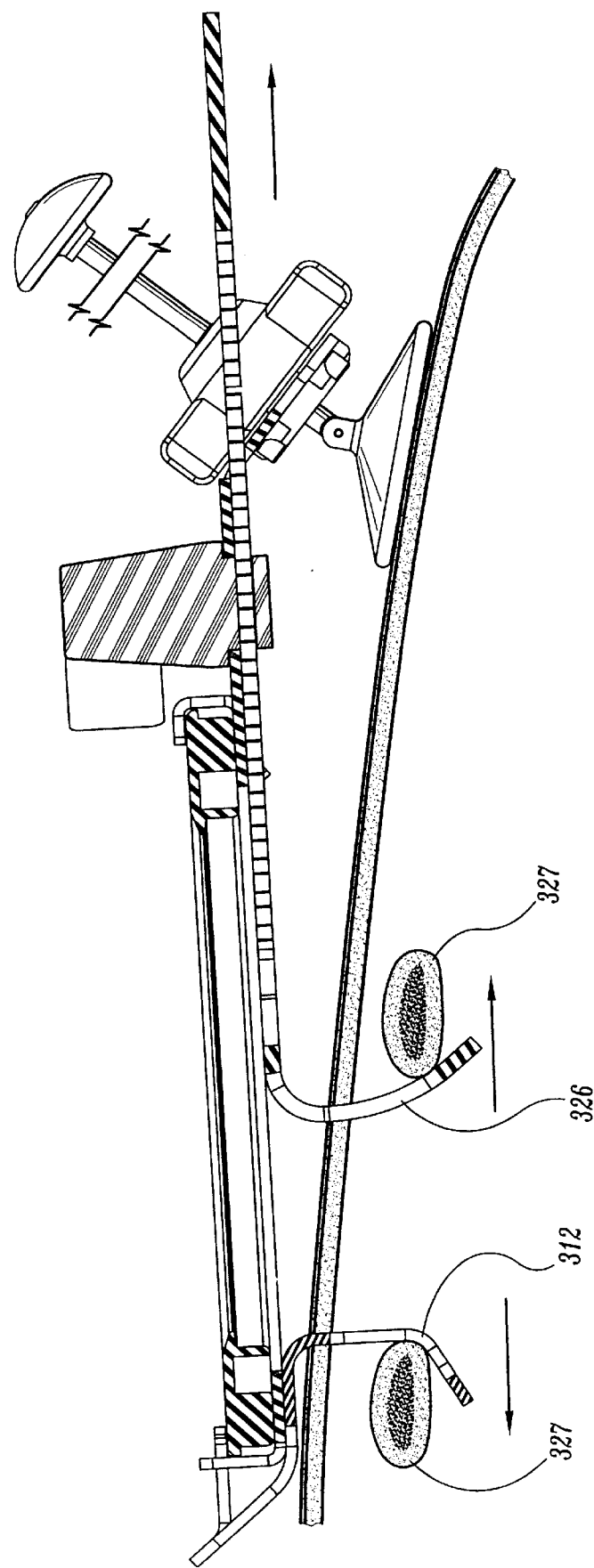
FIG. 26 is a cross-sectional view taken along line 25—25 of FIG. 24 of the surgical retractor positioned on the patient's chest, illustrating movement of the surgical retractor adjustable hook member to separate the patient's ribs.
Figure 27:
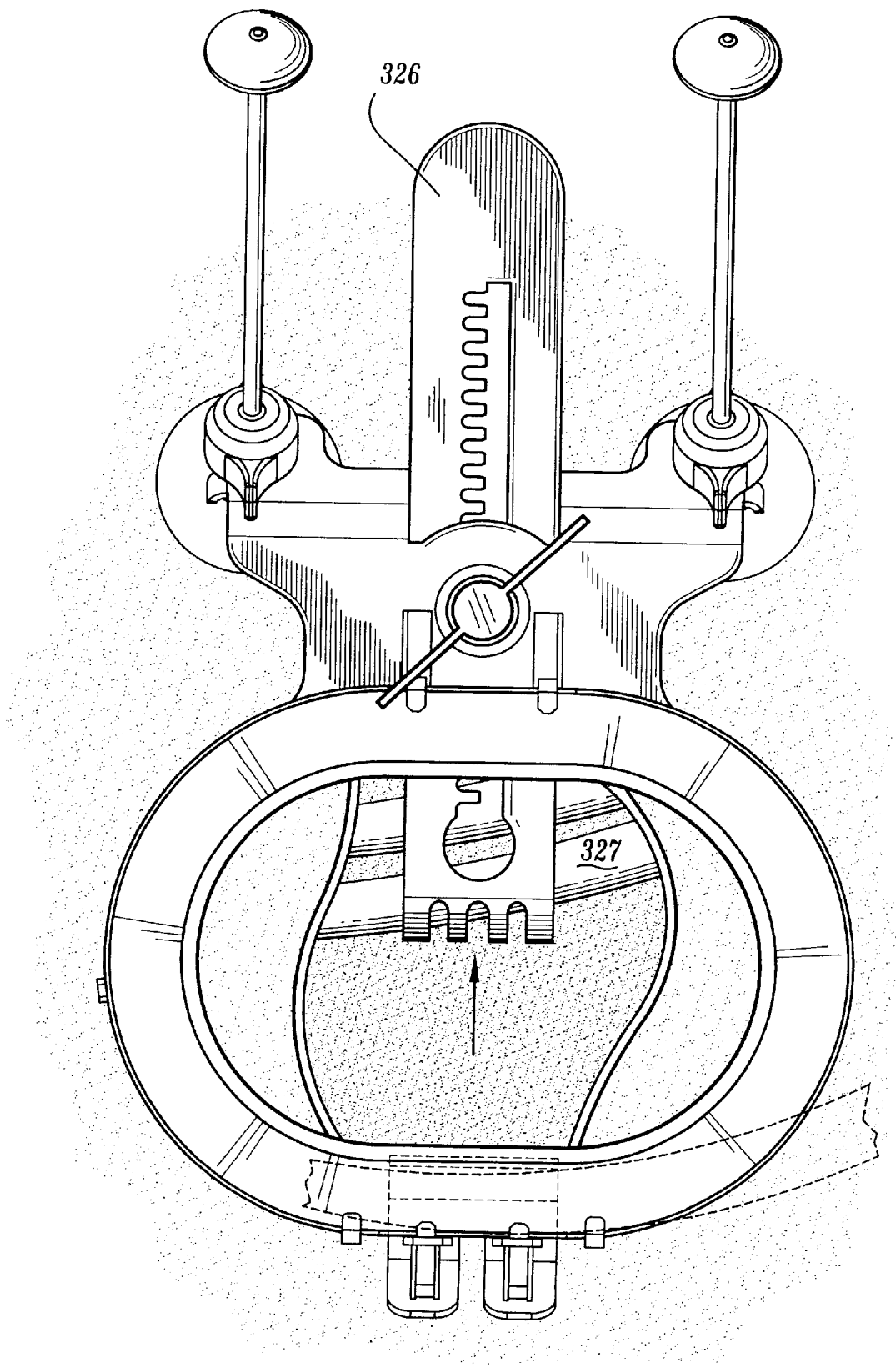
FIG. 27 is a top view illustrating the surgical retractor retracting the patient's ribs.

Referring now to FIGS. 24–27, conventional surgical techniques are used to determine the location of an incision for accessing the chest cavity. Surgical retractor 300 is then positioned on the patient's chest with the opening overlying the operative site. Once the ribs are exposed, adjustable hook 326 and hook portion 312 are positioned between two adjacent ribs 327 as illustrated in FIG. 25, and are subsequently moved in a manner to separate the ribs of the patient as illustrated in FIG. 26, thereby providing access to the heart as illustrated in FIG. 27. The operation of adjustable hook 326 is similar to that described above in connection with the embodiment of FIG. 1. Accordingly, that operation will not be described in further detail herein. Although the surgical retractor is illustrated and described with reference to a surgical procedure which provides access to the thoracic cavity by separating adjacent ribs, it is also contemplated that the surgical retractor may be used by the surgeon during a surgical procedure wherein the sternum must be separated.

Figure 28:
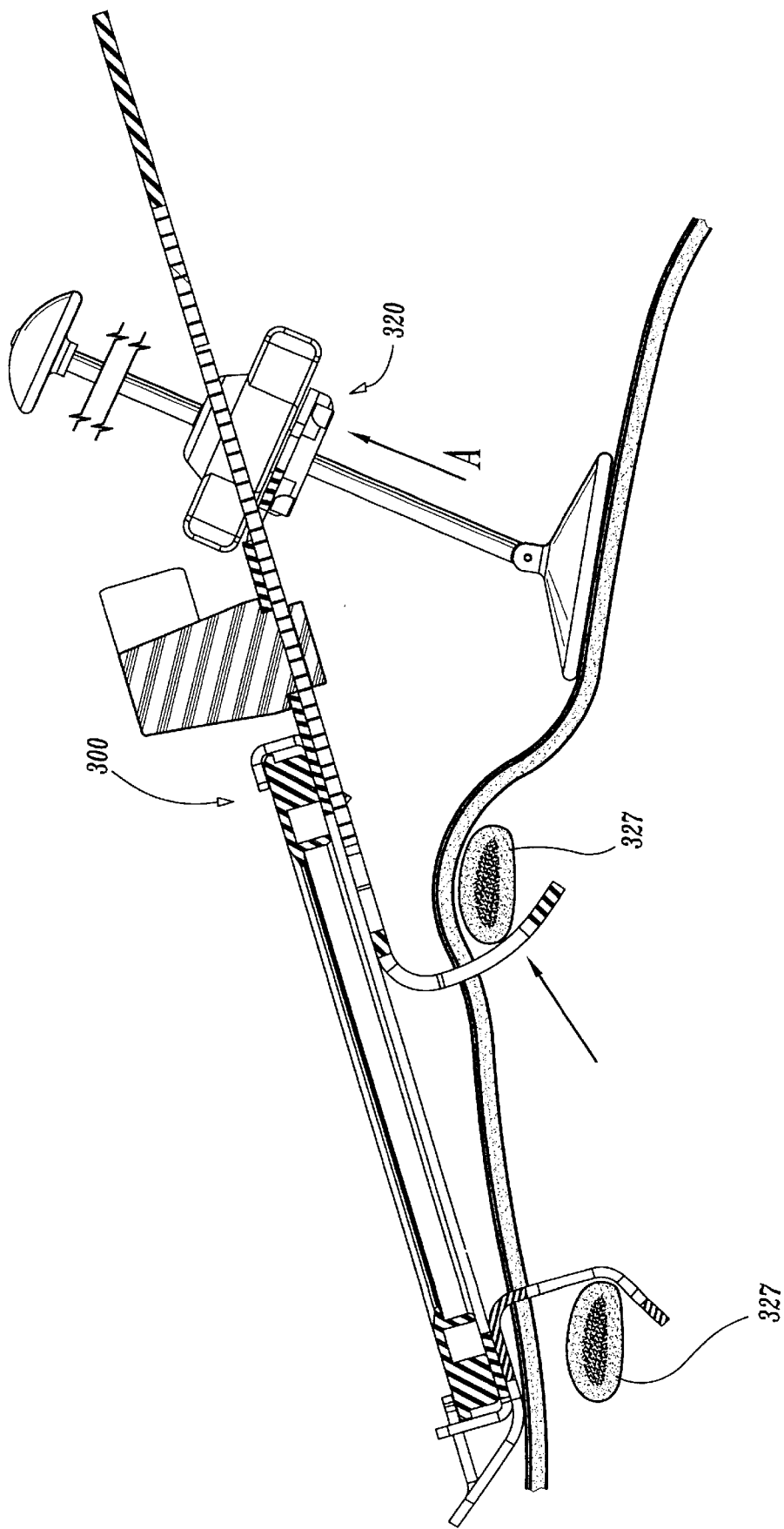
FIG. 28 is a cross-sectional view of the surgical retractor illustrating movement of the elevation control assembly to lift the patient's ribs.

Referring now to FIG. 28, to facilitate additional access to the thoracic cavity, elevation control assemblies 320 are adjusted to lift one side of surgical retractor 300 in the direction indicated by arrow A. The operation of elevation control assemblies 320 is similar to that described above in connection with the embodiment of FIG. 1. Accordingly, that operation will not be described in further detail herein.

Figure 30:
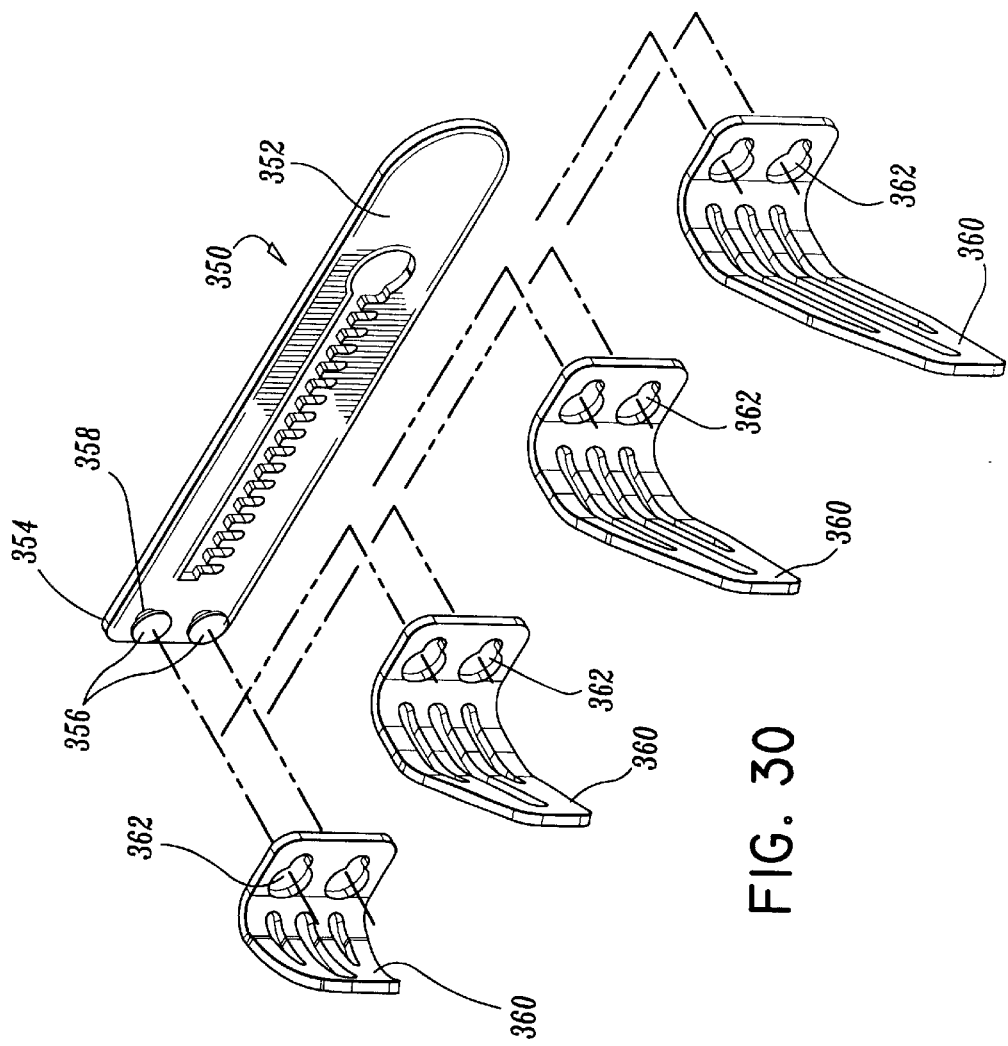
FIG. 30 is an exploded perspective view of the adjustable hook member illustrating different size hooks which may be used.
Figure 29:
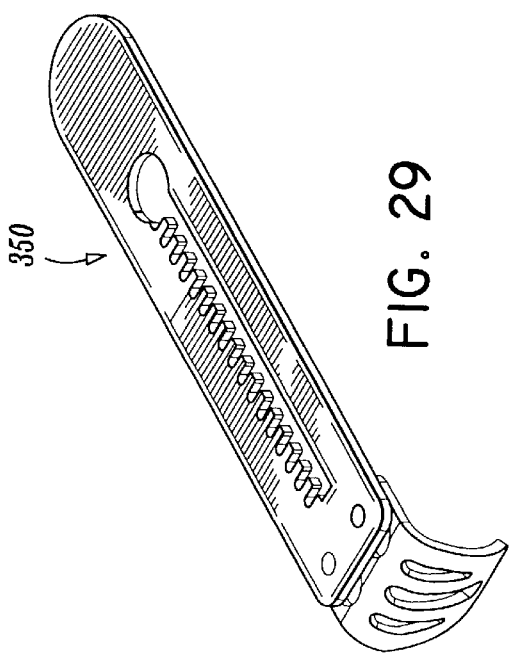
FIG. 29 is a perspective view illustrating another embodiment of the adjustable hook member in accordance with the present disclosure.

Referring now to FIGS. 29 and 30, an alternative embodiment of adjustable hook member 326, which is configured to receive different sized hooks, is illustrated. In this embodiment, the body portion 352 of adjustable hook member 350 includes two circular knobs 356 attached to a first end 354 thereof via two posts 358. Posts 358 have a smaller diameter than circular knobs 356 such that a gap region, which is slightly greater than the thickness of the plate material which forms hook members 360, is formed between circular knobs 356 and body portion 352. Hook members 360 include holes 362 formed therein. Holes 362 include a larger diameter portion which is slightly larger than the diameter of circular knobs 356, and a smaller diameter portion which is slightly larger that the diameter of posts 358. Therefore, hook member 360 may be removably attached to body portion 352 by placing the hook member over circular knobs 356 and pushing it toward end 354 of adjustable hook member 350 to lock it in position on posts 358. During operation of the surgical retractor, adjustable hook member 350 is moved in a direction which will assist in ensuring that hook member 360 remains attached to body portion 352.

Figure 31:
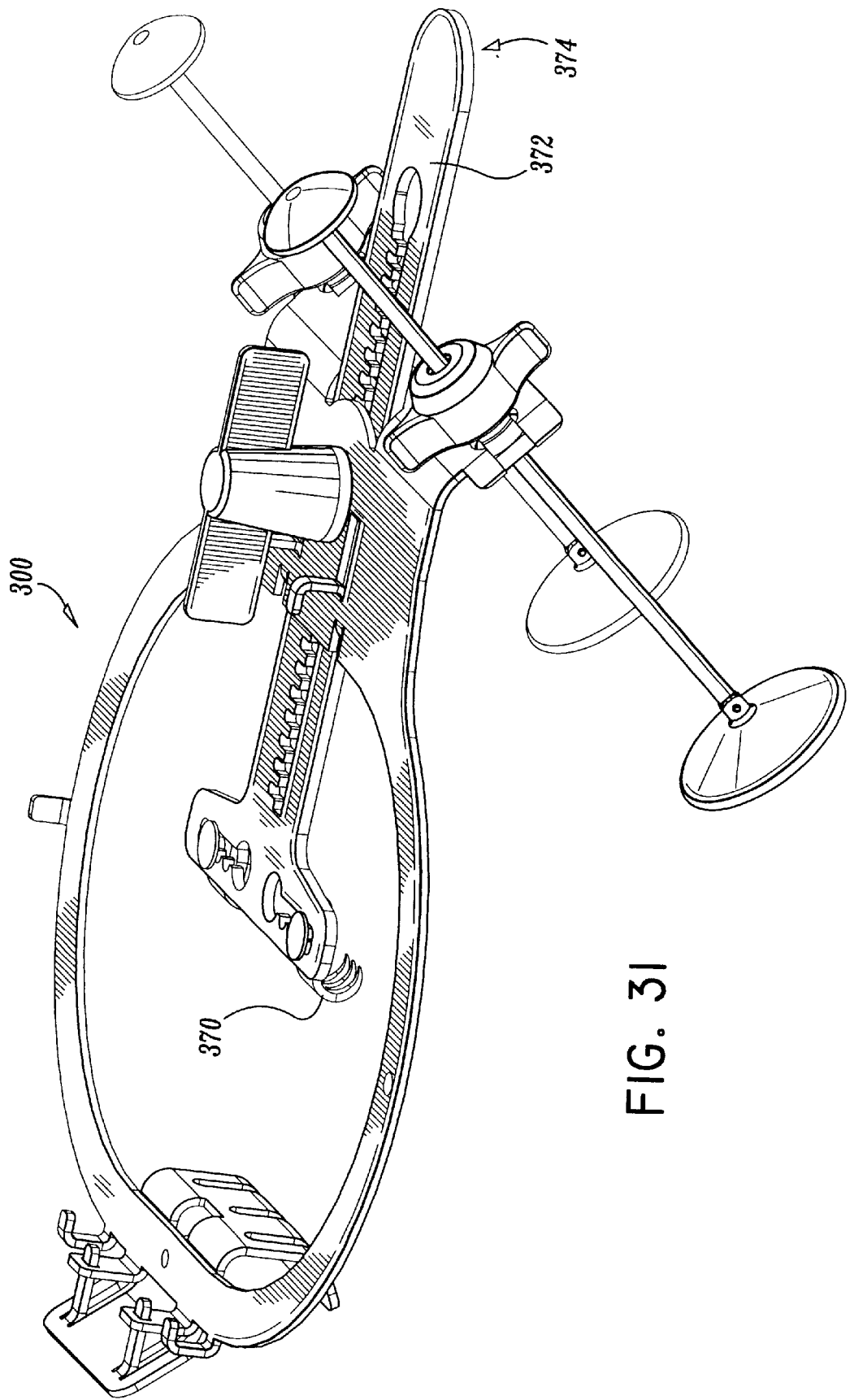
FIG. 31 is a perspective view of another embodiment of a surgical retractor in accordance with the present disclosure, having hooks which are advantageously designed to facilitate IMA take down procedures.
Figure 32:
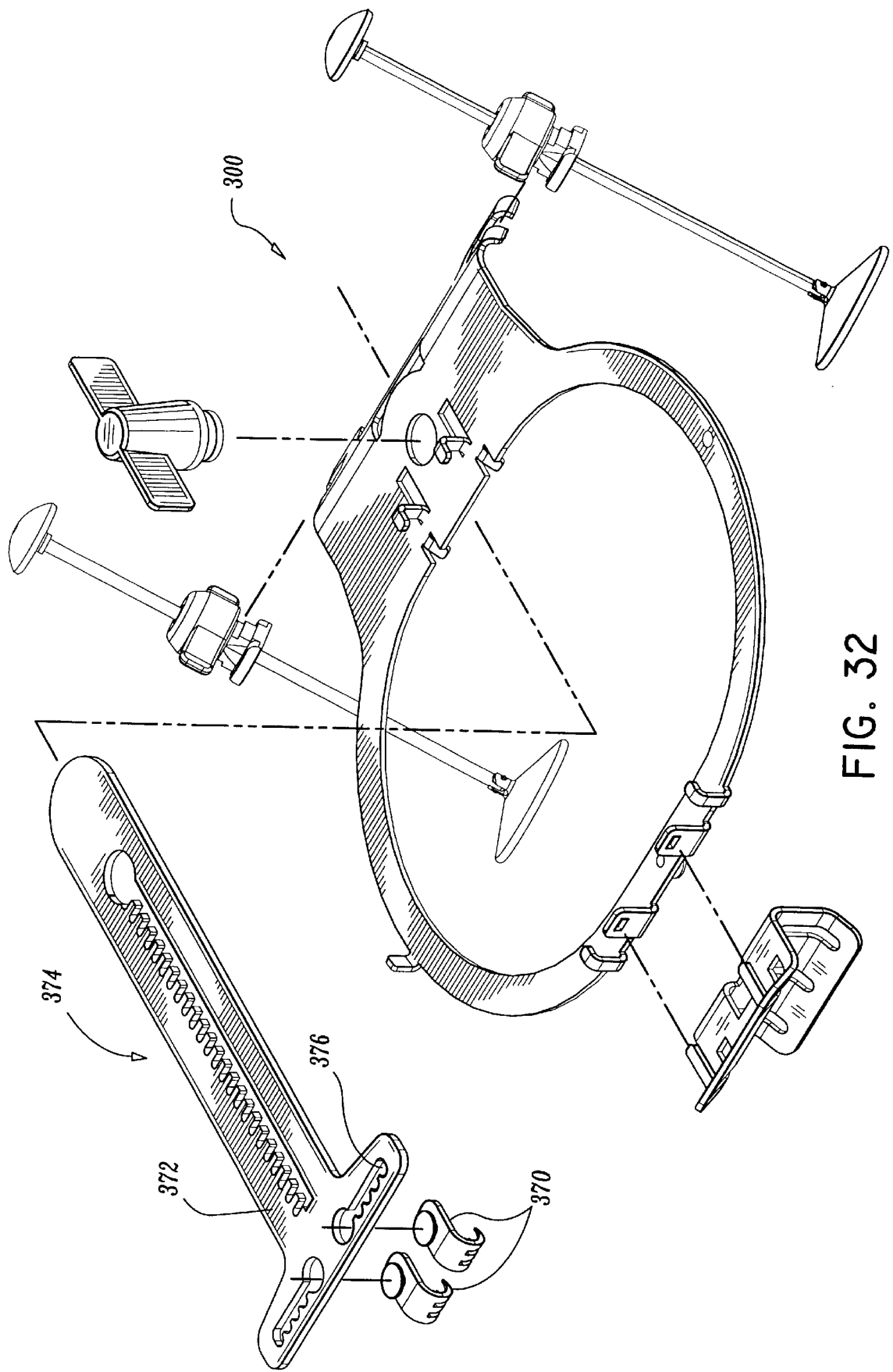
FIG. 32 is an exploded perspective view of the surgical retractor of FIG. 31.

Referring now to FIGS. 31 and 32, another embodiment of a surgical retractor 300 in accordance with the present disclosure is illustrated having hooks installed on the adjustable hook member which are advantageously designed to facilitate a surgical procedure known as an IMA takedown procedure. That is, during an IMA takedown procedure, it is often necessary to not only spread the ribs, but to lift them as well, to provide better access for the surgeon to the internal mammary artery. Accordingly, as illustrated in FIGS. 31 and 32, hook portions 370 are designed having a more pronounced curvature and pointed tips to facilitate a better hold on the skin and bones during the lifting motion. Hook portions 370 are attached to body portion 372 of adjustable hook member 374 in a similar manner as described above with reference to the embodiment in FIGS. 29 and 30. However, the reduced diameter portions of holes 376 in body portion 372, within which hook portions 370 are positioned, are elongated to facilitate adjustability of the spacing between the two hook portions. This will allow the surgeon to place hook portions 370 in a desired location to precisely spread and\or lift the patient's skin and\or bones. It is also contemplated that the embodiment illustrated in FIGS. 31 and 32 may be used by the surgeon during a surgical procedure wherein the sternum must be separated.

Figure 33:
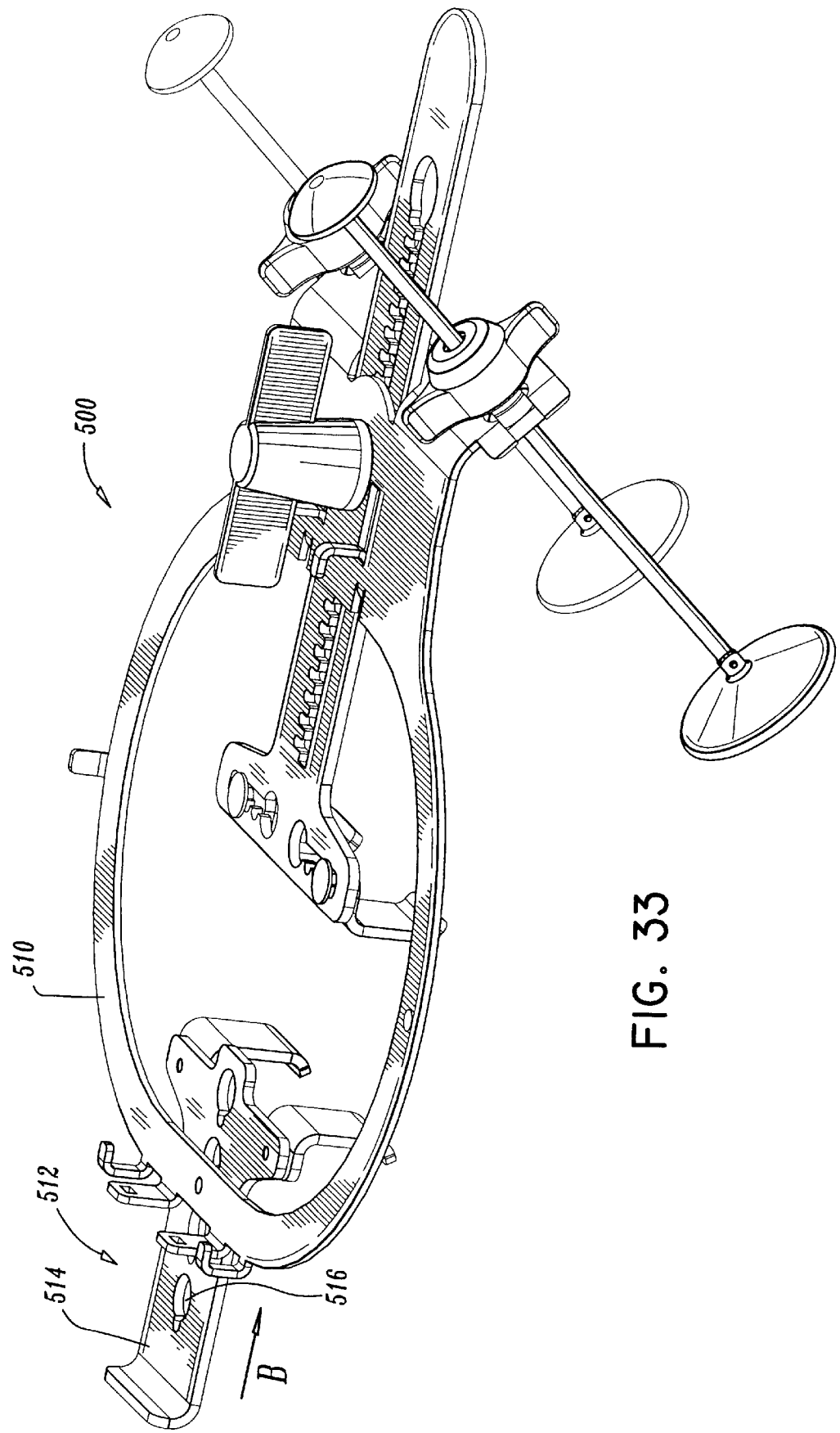
FIG. 33 is a perspective view of another embodiment of the surgical retractor in accordance with the present disclosure, having hooks which are advantageously designed to facilitate a bypass procedure.
Figure 34:
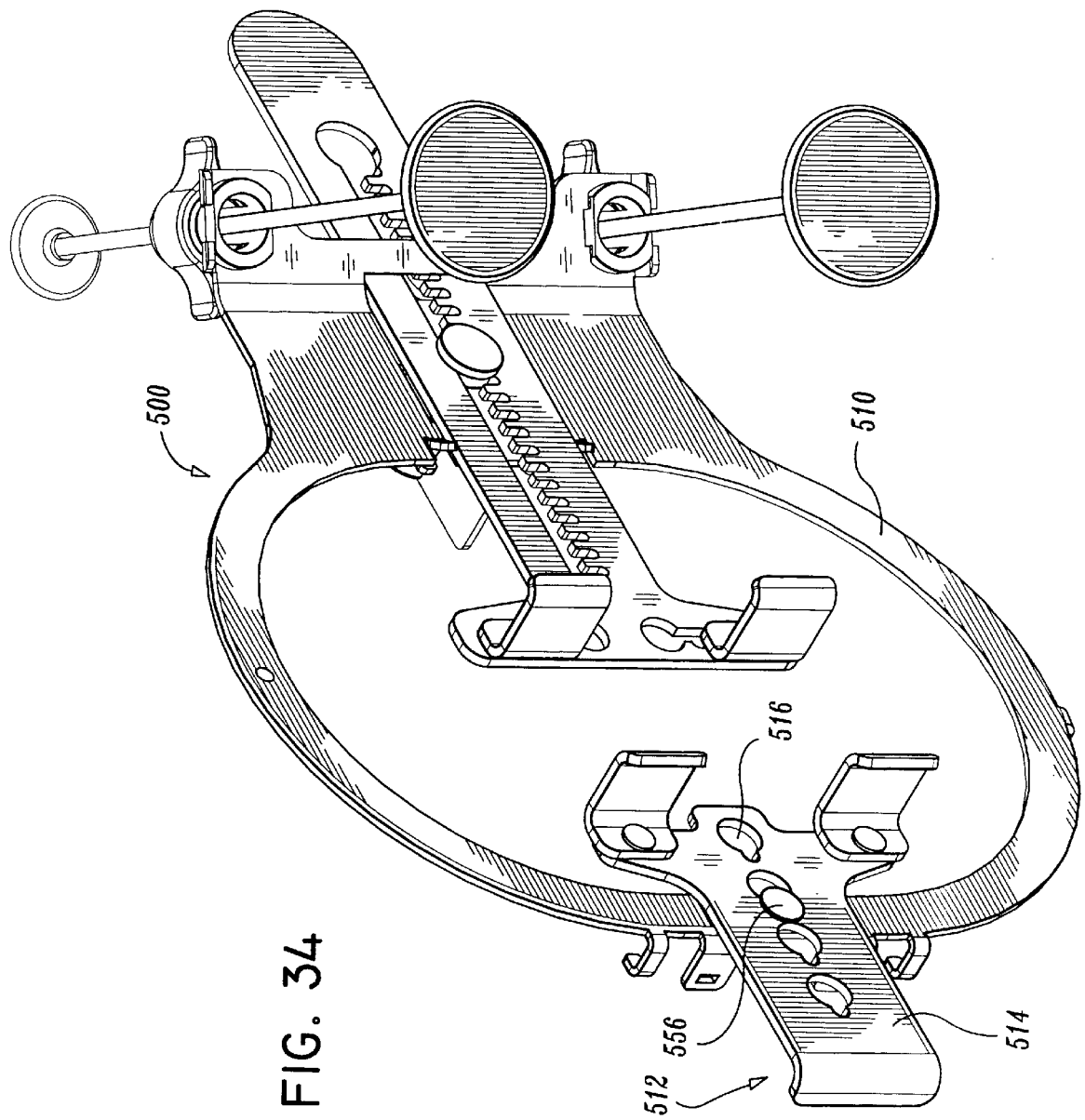
FIG. 34 is a bottom perspective view of the surgical retractor of FIG. 33.
Figure 35:
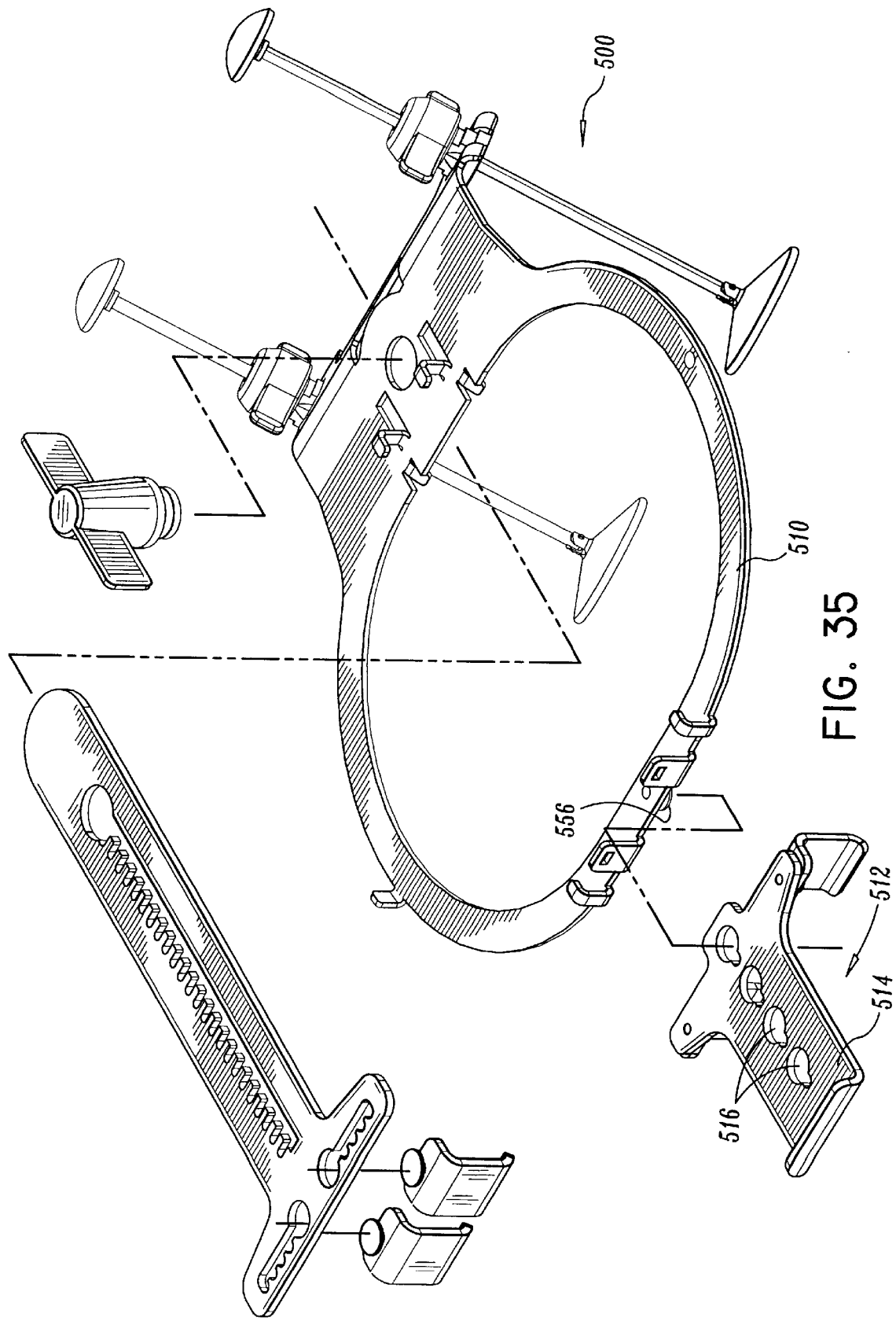
FIG. 35 is an exploded perspective view of the surgical retractor of FIG. 33.

Referring now to FIGS. 33–35, another embodiment of a surgical retractor 500 in accordance with the present disclosure is illustrated wherein the "fixed" hook assembly 512 may be removably attached to frame 510 in a plurality of different positions along the longitudinal axis of the hook assembly. The added ability to adjust the position of hook assembly 512 facilitates surgical procedures which require varying degrees of separation between the skin and bones of the patient to provide access for the surgeon.

As illustrated in FIGS. 33–35, a body portion 514 of hook assembly 512 includes a plurality of holes 516 along a longitudinal axis thereof. Holes 516 are configured to be mounted on frame 510 via a circular knob 556 and post attached thereto. The post has a smaller diameter than circular knob 556 such that a gap region, which is slightly greater than the thickness of the plate material which forms body portion 514 of hook assembly 512, is formed between circular knob 556 and frame 510. Holes 516 include a larger diameter portion which is slightly larger than the diameter of circular knob 556, and a smaller diameter portion which is slightly larger that the diameter of the post below knob 556. Therefore, body portion 514 may be removably and adjustably attached to frame 510 by placing the body portion over circular knob 556 at a position corresponding to one of holes 516, and pushing it toward the center of frame 510, as indicated by Arrow B in FIG. 33, to lock it in position on the posts within the smaller diameter portion of hole 516. During operation of the surgical retractor, hook assembly 512 is forced in the same direction (i.e., toward the center of frame 510) which will assist in ensuring that hook assembly 512 remains in a locked position and attached to frame 510. Body portion 514 is illustrated having four holes 516 therein. However, it is contemplated that more or less holes may be provided to vary the adjustability of hook assembly 512.

The remainder of the components of surgical retractor 500 are configured in a similar manner as described above with reference to at least one of the embodiments discussed above. Accordingly, the operation of these components will not be described in further detail herein.

Figure 36:
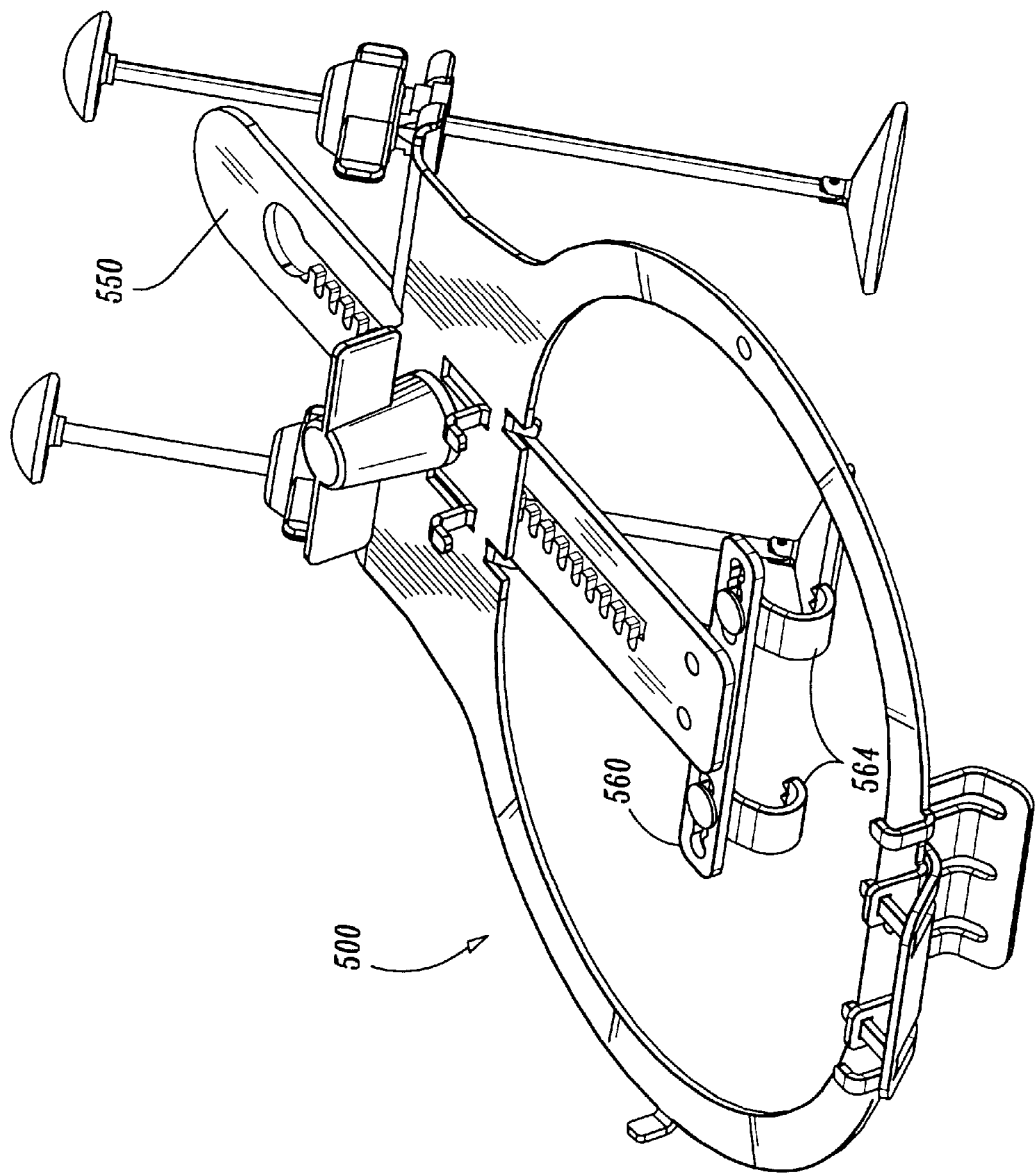
FIG. 36 is a perspective view of another embodiment of a surgical retractor in accordance with the present disclosure, having a removable cross-member and hooks on an end of the adjustable hook member.
Figures 37, 38:
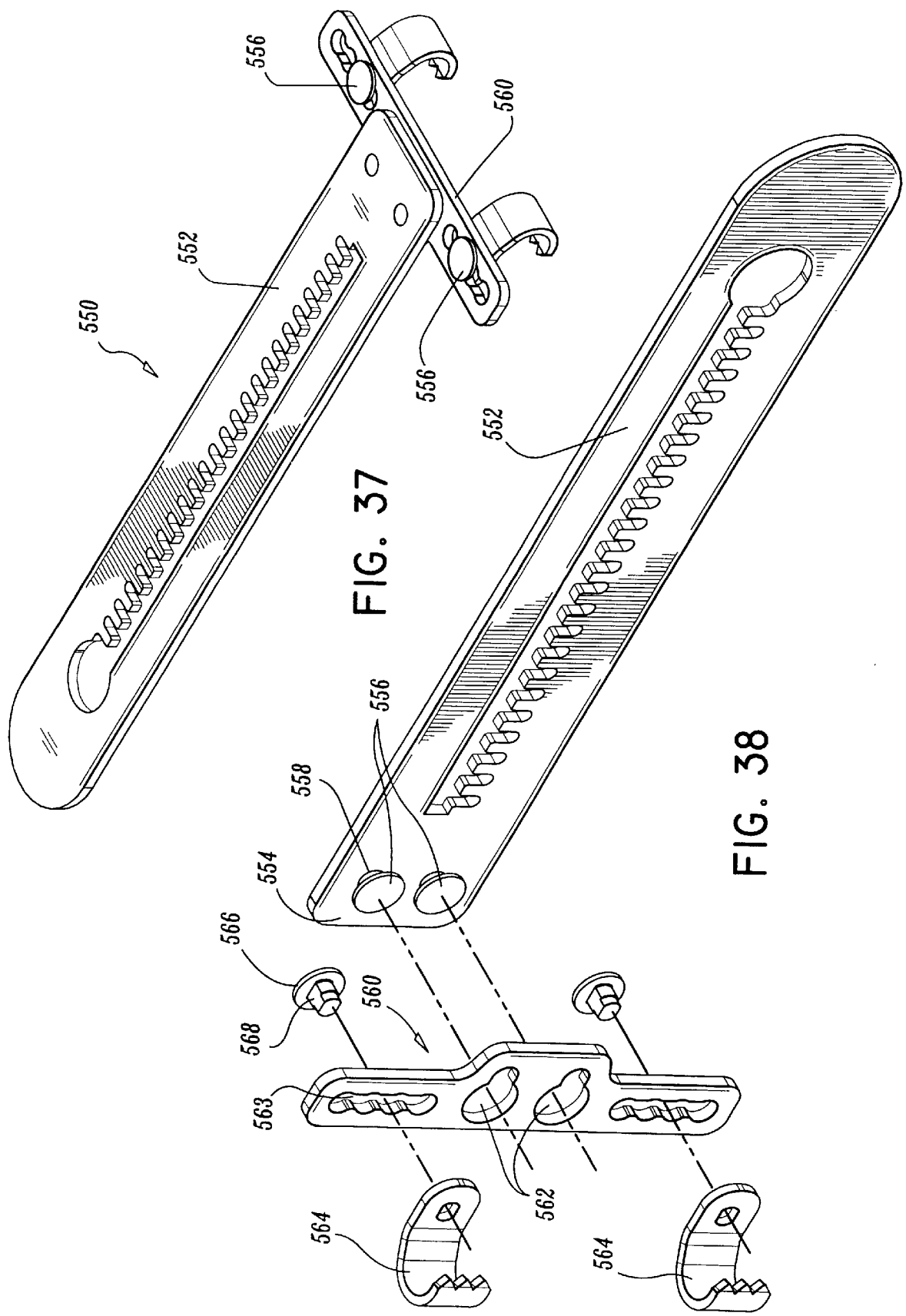
FIG. 37 is a perspective view of the adjustable hook member of FIG. 36.
FIG. 38 is an exploded perspective view of the adjustable hook member of FIG. 36.

Referring now to FIGS. 36–38, another embodiment of surgical retractor 500 in accordance with the present disclosure is illustrated wherein additional adjustability is provided in the configuration of adjustable hook member 550. In this embodiment, as best seen in FIGS. 37–38, the body portion 552 of adjustable hook member 550 includes two circular knobs 556 attached to a first end 554 thereof via two posts 558. Posts 558 have a smaller diameter than circular knobs 556 such that a gap region, which is slightly greater than the thickness of the plate material which forms cross-member 560, is formed between circular knobs 556 and body portion 552. Cross-member 560 includes holes 562 formed therein. Holes 562 include a larger diameter portion which is slightly larger than the diameter of circular knobs 556, and a smaller diameter portion which is slightly larger that the diameter of posts 558. Therefore, cross-member 560 may be removably attached to body portion 552 by placing the cross-member over circular knobs 556 and pushing it toward end 554 to lock it in position on posts 558. During operation of the surgical retractor, adjustable hook member 550 is moved in a direction which will assist in ensuring that cross-member 560 remains attached to body portion 552. Additionally, the smaller diameter portion of holes 562 may be dimensioned to provide an interference fit with posts 558 to facilitate the attachment of cross-member 560 to body portion 552.

Cross-member 560 further includes two elongated holes 563 to provide additional adjustability of the spacing between the two hook portions 564. Hook portions 564 are removably connected to cross-member 560 via circular knobs 566 and posts 568 in a similar manner as cross-member 560 is connected to body portion 552. Elongate holes 563 have a substantially sinusoidal perimeter which forms a plurality of defined individual openings for receiving receiving posts 568. Posts 568 have a substantially double-D cross-section to facilitate locking the posts 568 within the individual openings, while retaining the ability to move the post to an adjacent individual opening by rotating the post approximately ninety degrees and sliding it along the slot formed by elongate hole 563. Post 568 is then rotated ninety degrees to lock it in position to prevent inadvertent shifting during use.

Figure 39:
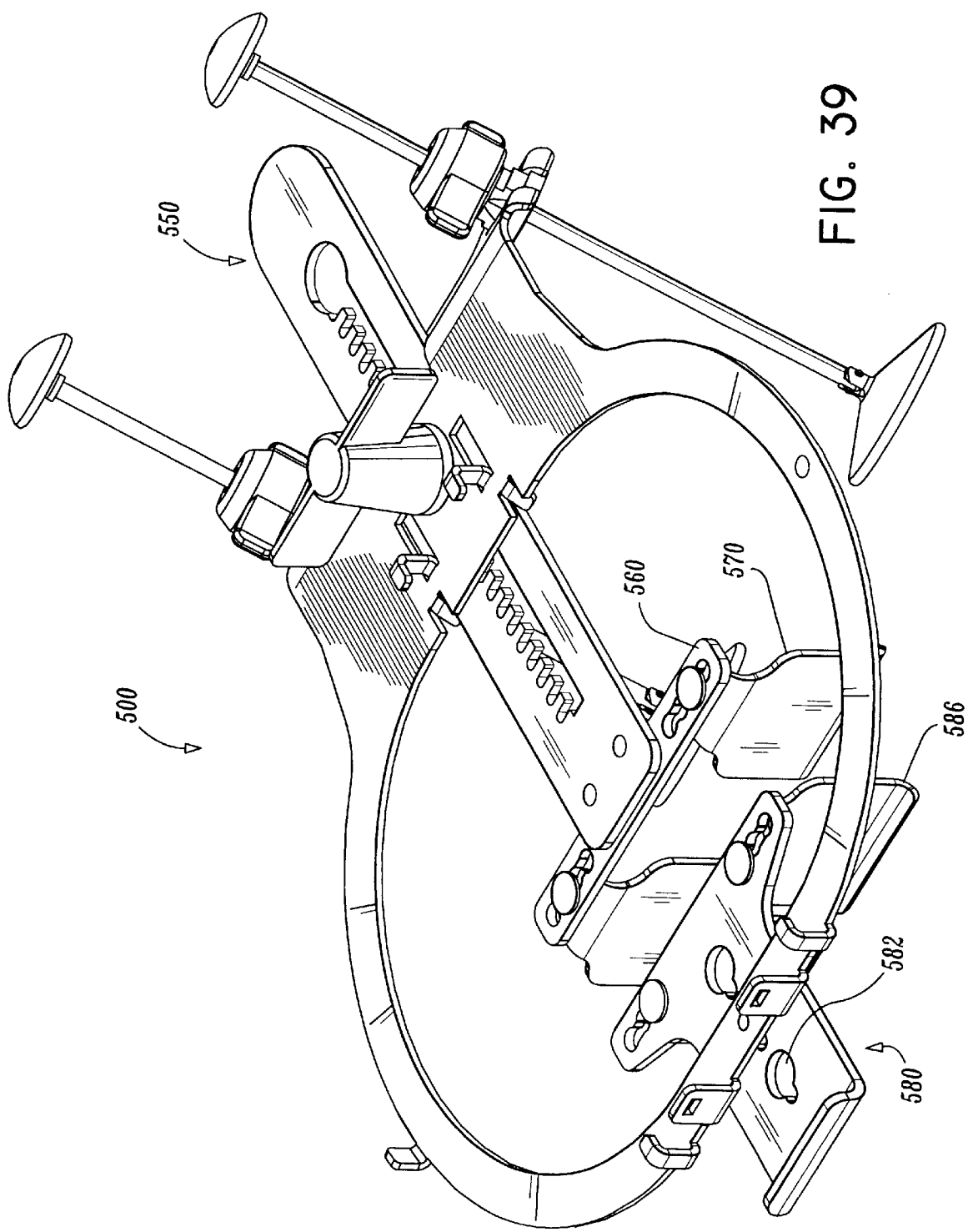
FIG. 39 is a perspective view of another embodiment of a surgical retractor in accordance with the present disclosure, having a removable cross-member and hooks on an end of the adjustable hook member and an adjustably fixed hook member.
Figure 40:
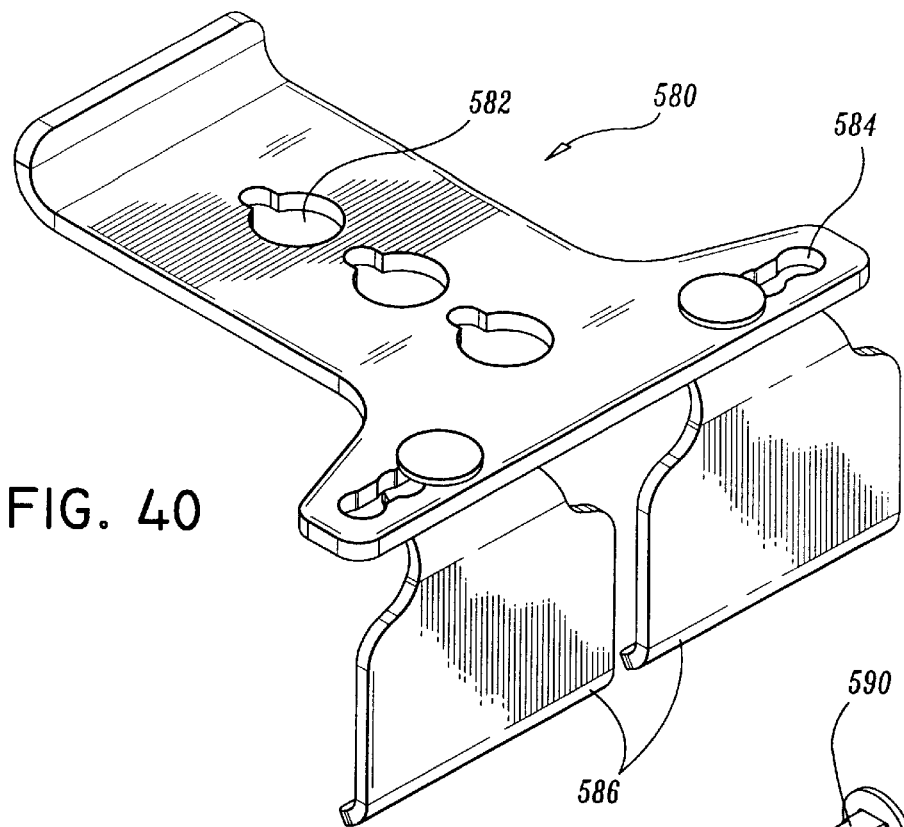
FIG. 40 is a perspective view of the adjustably fixed hook member of FIG. 39.
Figure 41:
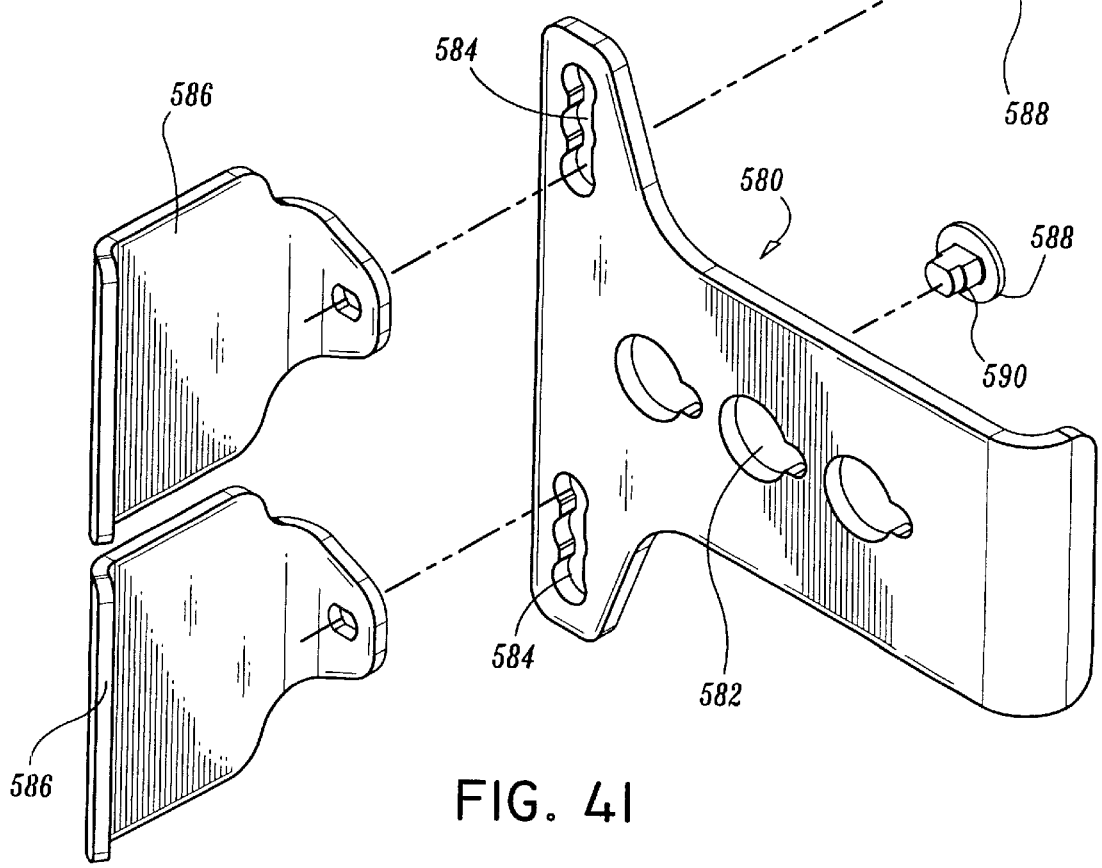
FIG. 41 is an exploded perspective view of the adjustably fixed hook member of FIG. 39.
Figure 42:
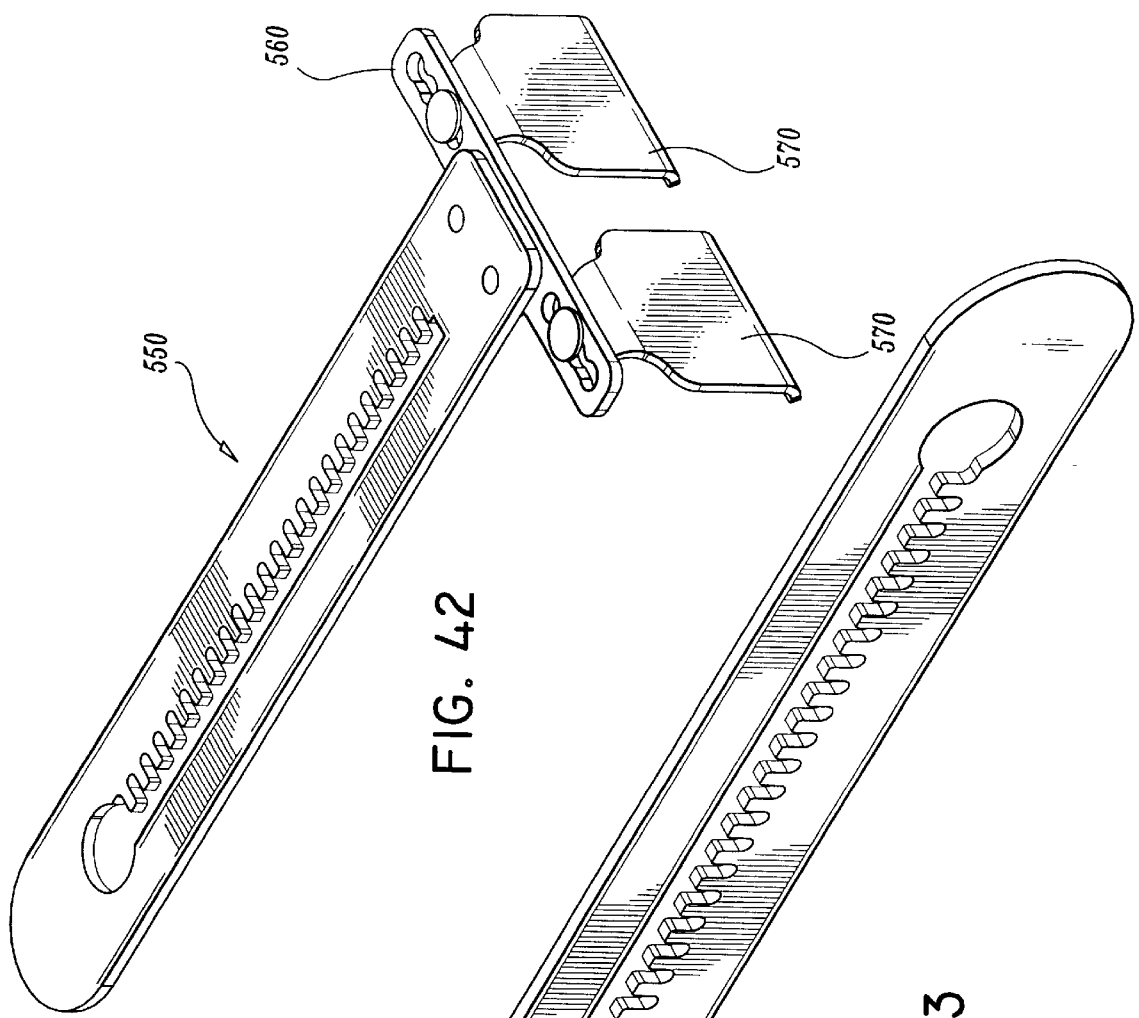
FIG. 42 is a perspective view of the adjustable hook member of FIG. 39.
Figure 43:
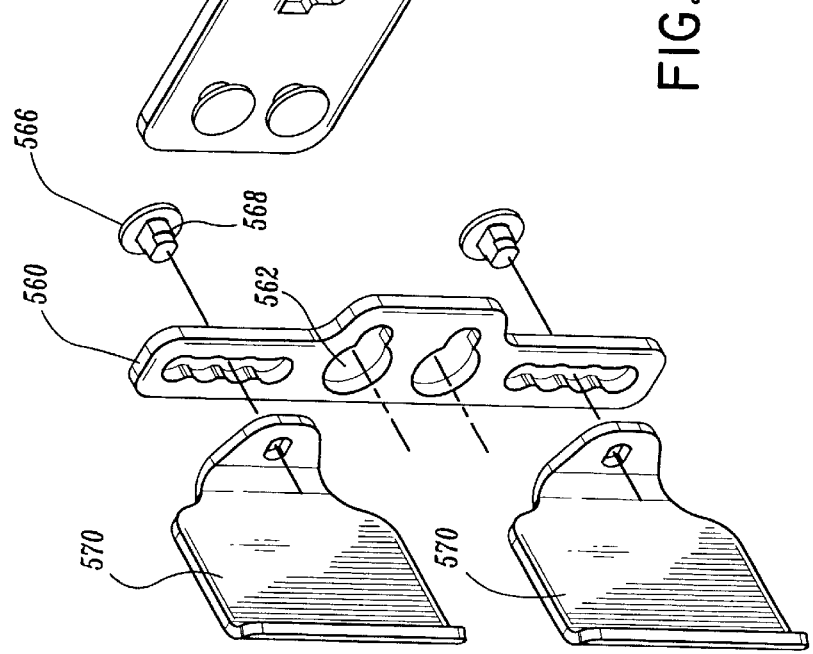
FIG. 43 is an exploded perspective view of the adjustable hook member of FIG. 39.

Referring now to FIGS. 39–43, another embodiment of a surgical retractor in accordance with the present disclosure is illustrated having a removable cross-member and hooks on an end of the adjustable hook member and an adjustably fixed hook member. The embodiment of surgical retractor 500 which is illustrated in FIGS. 39–43 incorporates each of the adjustability features discussed above with reference to the prior embodiments. More specifically, the adjustable hook member is similar to adjustable hook member 550 described above with respect to the embodiment illustrated in FIG. 36. The removable cross-member and hooks advantageously give the surgeon the option of using different types of hook portions for different surgical procedures. For example, as illustrated in FIGS. 39 and 42–43, hook portions 570 having a substantially flat shape may be substituted for hook portions which have a substantially curved shape, when the surgeon needs to spread the cavity rather than lift a portion of the patient's skin or bones.

The "fixed" hook member 580 incorporates the adjustability features of hook member 512 illustrated in FIGS. 33–35, wherein a plurality of holes 582 are formed along a longitudinal axis thereof to facilitate removable and adjustable attachment to frame 510. Furthermore, hook member 580 includes two elongated holes 584 to provide additional adjustability of the spacing between the two hook portions 586. Hook portions 586 are removably connected to hook member 580 via circular knobs 588 and posts 590 in a similar manner as described above.

It will be understood that various modifications may be made to the embodiment shown herein. Therefore, the above description should not be construed as limiting, but merely as exemplifications of preferred embodiments. Those skilled in the art will envision other modifications within the scope and spirit of the presently disclosed surgical retractor.

What is claimed is:

1. A surgical retractor assembly comprising:
   a frame lying in a first plane, the frame supporting at least one hook member configured to retract at least one of tissue and bone;
   at least one elevation control assembly supporting the frame, the elevation control assembly configured to selectively retain at least a portion of the frame out of the first plane; and
   a ring member removably mounted on the frame, the ring member configured to engage at least one surgical instrument for use in performing a surgical procedure.

2. The surgical retractor assembly of claim 1 wherein the at least one hook member is integral with the frame.

3. The surgical retractor assembly of claim 1, wherein at least one hook member is removably mounted on the frame.

4. The surgical retractor assembly of claim 1 wherein the at least one hook member is movable with respect to the frame.

5. The surgical retractor assembly of claim 4, further comprising an adjustment knob for moving the at least one hook member with respect to the frame.

6. The surgical retractor assembly of claim 5, wherein the at least one hook member has a plurality of teeth engageable by the adjustment knob.

7. The surgical retractor assembly of claim 1 wherein the at least one hook member includes a body portion and at least one hook portion.

8. The surgical retractor assembly of claim 7 wherein the at least one hook portion is removably mounted on the body portion.

9. The surgical retractor assembly of claim 7 wherein the at least one hook portion is integral with the body portion.

10. The surgical retractor assembly of claim 1, wherein the frame and the ring member are substantially oval in configuration.

11. The surgical retractor assembly of claim 1, wherein the frame and the ring member define an opening for allowing access to a patient's body therethrough.

12. The surgical retractor assembly of claim 1, further comprising a second hook member removably mounted on the frame and movable to retract at least one of tissue and bone in a direction away from the at least one hook member.

13. The surgical retractor assembly of claim 1, wherein the at least one elevation control assembly comprises an elongated shaft having a locking mechanism to retain the frame in a selected position.

14. The surgical retractor assembly of claim 1, wherein the at least one elevation control assembly includes a pair of elongated shafts removably mounted to the frame, each of the elongated shafts including a locking assembly to retain the frame in a selected position.

15. The surgical retractor assembly of claim 14, wherein each locking assembly includes a collet and a compressible member mounted on the shaft, the collet configured to compress the compressible member onto the shaft.

16. A method for accessing the thoracic cavity of a patient in a minimally invasive surgical procedure comprising the steps of:
   making an incision in the patient's chest to expose the ribs;
   placing a frame of a surgical retractor assembly on the patient's chest such that an opening defined by the frame surrounds the intended opening to the thoracic cavity;
   placing a first hook member supported on the frame between two adjacent ribs;
   placing a second hook member supported on the frame between the two adjacent ribs;
   moving the second hook member in a direction away from the first hook member to retract the ribs;
   attaching a ring member to the frame; and
   attaching at least one surgical instrument to the ring member to facilitate a surgical procedure within the opening to the thoracic cavity.

17. The method of claim 16, further comprising the steps of:
   elevating a first portion of the frame away from the patient's chest to a selected raised position; and
   retaining the first portion of the frame in the selected raised position.

18. The method of claim 17, wherein the step of elevating the first portion of the frame comprises the step of manually sliding the first portion along first and second spaced apart shafts.

19. The method of claim 17, wherein the step of retaining the first portion comprises the step of compressing a compressible member against each of the shafts.

20. The method of claim 16, wherein the step of moving the second hook member comprises rotating an adjustment knob.

21. A surgical retractor assembly comprising:

a frame lying in a plane;

a first hook assembly movably supported on the frame and configured to retract a first portion of at least one of tissue and bone from a second portion of at least one of tissue and bone;

a second hook assembly repositionably mounted in a fixed position on the frame at a location opposite to the first hook assembly and configured to maintain the second portion of at least one of tissue and bone in a fixed position relative to the first portion of at least one of tissue and bone to facilitate retraction of the first portion from the second portion;

at least one elevation control assembly supporting the frame, the elevation control assembly configured to selectively retain at least a portion of the frame out of the plane; and a ring member removably mounted on the frame, the ring member configured to engage at least one surgical instrument for use in performing a surgical procedure.

22. The surgical retractor assembly of claim 21 wherein the first hook assembly has at least two holes formed in an end portion thereof to removably receive at least two hook members.

23. The surgical retractor assembly of claim 22, wherein the at least two holes are elongate to facilitate adjustability of a space between the at least two hook members.

24. The surgical retractor assembly of claim 21 wherein the second hook assembly has a plurality of holes formed in a longitudinal axis thereof for repositionably mounting the second hook member in a corresponding plurality of positions on the frame.

25. The surgical retractor assembly of claim 21 wherein the second hook assembly has at least two holes formed in an end portion thereof to removably receive at least two hook members.

26. The surgical retractor assembly of claim 25, wherein the at least two holes are elongate to facilitate adjustability of a space between the at least two hook members.

* * * * *